(12) United States Patent
Schulman et al.

(10) Patent No.: US 6,472,991 B1
(45) Date of Patent: Oct. 29, 2002

(54) MULTICHANNEL COMMUNICATION PROTOCOL CONFIGURED TO EXTEND THE BATTERY LIFE OF AN IMPLANTABLE DEVICE

(75) Inventors: Joseph H. Schulman, Santa Clarita, CA (US); John C. Gord, Venice, CA (US); Paul D. DeRocco, Pacific Palisades, CA (US); Lawrence J. Karr, Santa Monica, CA (US); Dan Folkman, Valencia, CA (US); Andrew Barber, Los Angeles, CA (US)

(73) Assignee: Alfred E. Mann Foundation for Scientific Research, Valencia, CA (US)

( * ) Notice: Subject to any disclaimer, the term of this patent is extended or adjusted under 35 U.S.C. 154(b) by 0 days.

(21) Appl. No.: 09/882,603

(22) Filed: Jun. 15, 2001

(51) Int. Cl.[7] ................................................ G08B 21/00
(52) U.S. Cl. ............................ 340/636; 340/635; 607/2; 607/16
(58) Field of Search ................................. 340/635, 636; 128/898, 899, 903, 904; 604/20, 21, 890.1, 891.1; 607/1, 2, 4, 9, 16

(56) References Cited

U.S. PATENT DOCUMENTS

| | | | |
|---|---|---|---|
| 4,592,360 A | 6/1986 | Lesnick | |
| 5,324,316 A | 6/1994 | Schulman et al. | |
| 5,843,139 A | 12/1998 | Goedeke et al. | |
| 5,954,755 A | 9/1999 | Casavant | |
| 5,994,880 A | * 11/1999 | Dropps | 320/140 |
| 5,999,848 A | 12/1999 | Gord et al. | |
| 6,101,417 A | * 8/2000 | Vogel et al. | 607/30 |
| 6,164,284 A | 12/2000 | Schulman et al. | |
| 6,185,452 B1 | 2/2001 | Schulman et al. | |
| 6,185,454 B1 | * 2/2001 | Thompson | 607/2 |
| 6,239,724 B1 | * 5/2001 | Doron et al. | 340/870.28 |

* cited by examiner

Primary Examiner—Van Trieu
(74) Attorney, Agent, or Firm—Lee J. Mandell

(57) ABSTRACT

A communication protocol that is configured to extend the battery life of devices that monitor and/or affect body parameters and is particularly useful in a system comprised of a system control unit (SCU) and one or more implanted devices. Each such implanted device is configured to be monitored and/or controlled by the SCU via a wireless communication channel. The time between battery rechargings is determined by the battery capacity and the device's power consumption. Accordingly, the present invention reduces their average power consumption by reducing the usage duty cycle of their power consuming transmit and receive modes used to communicate with the SCU. By dedicating addressable time slots to each of the implantable devices in the system and limiting their use of receive and transmit modes to time periods proximate to these time slots, the average power consumption is accordingly reduced.

58 Claims, 16 Drawing Sheets

OPEN LOOP CONTROL/MONITOR

CLOSED LOOP CONTROL

EXEMPLARY INJURY

COORDINATED CLOSED LOOP HAND CONTROL

MULTICHANNEL COMMUNICATION PROTOCOL CONFIGURED TO EXTEND THE BATTERY LIFE OF AN IMPLANTABLE DEVICE

FIELD OF THE INVENTION

The present invention is generally directed to implantable medical devices and in particular battery-powered implantable medical devices and systems for communicating with such devices.

BACKGROUND OF THE INVENTION

The present invention relates to systems for monitoring and/or affecting parameters of a patient's body for the purpose of medical diagnosis and/or treatment. More particularly, systems in accordance with the invention are characterized by a plurality of devices, preferably battery powered, configured for implanting within a patient's body, each device being configured to sense a body parameter, e.g., temperature, $O_2$ content, physical position, electrical potential, etc., and/or to affect a parameter, e.g., via nerve and/or muscle stimulation.

Commonly owned U.S. Pat. No. 6,164,284 entitled "System of Implantable Devices For Monitoring and/or Affecting Body Parameters" and U.S. Pat. No. 6,185,452 entitled "Battery Powered Patient Implantable Device", incorporated herein by reference in their entirety, describe devices configured for implantation within a patient's body, i.e., beneath a patient's skin, for performing various functions including: (1) stimulation of body tissue and/or sensing of body parameters, and (2) communicating between implanted devices and devices external to a patient's body. Depending upon the ailment affecting the patient, it may be desirable to communicate with a number of different devices, e.g., from one to thousands, while maintaining an update rate, e.g., on the order of every 1 millisecond to every second, sufficient to control and/or monitor the body parameter(s) at issue. Such implantable devices are preferably powered using rechargeable batteries. Depending on the power requirements of these devices and the available capacity of their rechargeable batteries, the time between rechargings is potentially limited. Accordingly, power conservation techniques to extend the battery life of such devices are desirable. The present invention is directed to a multichannel communication system and protocol that facilitate such power conservation while maintaining the required update rate.

SUMMARY OF THE INVENTION

The present invention is directed to a communication system and protocol that is configured to extend the battery life of battery-powered devices that monitor and/or affect parameters of a patient's body and is particularly useful in a system comprised of a system control unit (SCU) and one or more devices implanted in the patient's body, i.e., within the envelope defined by the patient's skin. Each such implanted device is configured to be monitored and/or controlled by the SCU via a wireless communication channel.

In accordance with the invention, the SCU comprises a programmable unit capable of (1) transmitting commands to at least some of a plurality of implanted devices and (2) receiving data signals from at least some of those implanted devices. In accordance with a preferred embodiment, the system operates in closed loop fashion whereby the commands transmitted by the SCU are dependent, in part, on the content of the data signals received by the SCU.

In accordance with an exemplary embodiment, each implanted device is configured similarly to the devices described in the commonly owned U.S. Pat. No. 6,164,284 and typically comprises a sealed housing suitable for injection into the patient's body. Each housing preferably contains a power source having a capacity of at least 1 microwatt-hour and power consuming circuitry preferably including a data signal transmitter and receiver and sensor/stimulator circuitry for driving an input/output transducer. Wireless communication between the SCU and the other implanted devices can be implemented in various ways, e.g., via a modulated sound signal, an AC magnetic field, an RF signal, a propagated electromagnetic wave, a light signal, or electrical conduction.

Preferably such implantable devices are powered by an internal rechargeable battery. The amount of time between rechargings of the battery is determined by the battery capacity and the power consumption of the device. The present invention reduces the average power consumption of the implantable devices by reducing the usage duty cycle of the power consuming transmit and receive modes used by the implantable devices to communicate with the SCU while maintaining a sufficient update rate to control and/or monitor the required body parameter(s). By dedicating addressable time slots to each of the implantable devices in the system and limiting their use of receive and transmit modes to time periods proximate to these time slots, the average power consumption is accordingly reduced.

In accordance with the present invention, a preferred method is described for communicating between a system controller and a plurality of addressable, battery-powered, implantable stimulation/sensor devices that is configured to extend the battery life of the implantable devices by reducing their average power consumption. In the preferred method, the system controller periodically, during a system control data time period, sends a system control data message which defines addressable data that is to be directed to each of the plurality of implantable devices, wherein the implantable devices consume a base amount of power and additionally consume a first incremental amount of power when operating in a receive mode to receive data from the system controller during a selected portion of the system control data time period, the selected portion of the system control data time period being a portion, i.e., less than 75%, of the system control data time period and the average power consumption of the implantable devices is reduced accordingly. The system controller then waits a response time period following each system control data message for enabling each of the implantable devices to provide data to the system controller in a selected portion of the response time period related to the address of each implantable device, wherein the implantable devices additionally consume a second incremental amount of power when operating in the transmit mode, the selected portion of the response time period being a portion, i.e., less than 75%, of the response time period and the average power consumption of the implantable devices is reduced accordingly.

In accordance with a further aspect of the invention, the implantable devices are configurable to switch between a first mode of operation where the selected portion of the response time period is used for responses from a single implantable device and a second mode of operation where the selected portion of the response time period is alternately shared for sending responses to the system controller from a plurality of implantable devices, thereby extending the battery life of the implantable devices that share the selected time response period portions.

In a still further aspect of the present invention at least one selected implantable device is configurable via data within the system control data message to occupy a plurality of the selected portions of the response time period to thereby increase the effective communication rate from the selected implantable device to the system controller.

The novel features of the invention are set forth with particularity in the appended claims. The invention will be best understood from the following description when read in conjunction with the accompanying drawings.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

The present invention is directed to a system for monitoring and/or affecting parameters of a patient's body and more particularly to such a system comprised of a system control unit (SCU) and one or more devices implanted in a patient's body, i.e., within the envelope defined by the patient's skin. Each such implantable device is configured to be monitored and/or controlled by the SCU via a wireless communication channel.

In accordance with the invention, the SCU comprises a programmable unit capable of (1) transmitting commands to at least some of a plurality of implanted devices and (2) receiving data signals from at least some of those implanted devices. In accordance with a preferred embodiment, the system operates, at least in part, in closed loop fashion whereby the commands transmitted by the SCU are dependent, in part, on the content of the data signals received by the SCU.

In accordance with a preferred embodiment, each implanted device is configured similarly to the devices described in the commonly owned U.S. Pat. No. 6,164,284 (hereinafter referred to as the '284 patent) and typically comprises a sealed housing suitable for injection into the patient's body. Each housing preferably contains a power source having a capacity of at least 1 microwatt-hour, preferably a rechargeable battery, and power consuming circuitry preferably including a data signal transmitter and receiver and sensor/stimulator circuitry for driving an input/output transducer.

Figure 1:
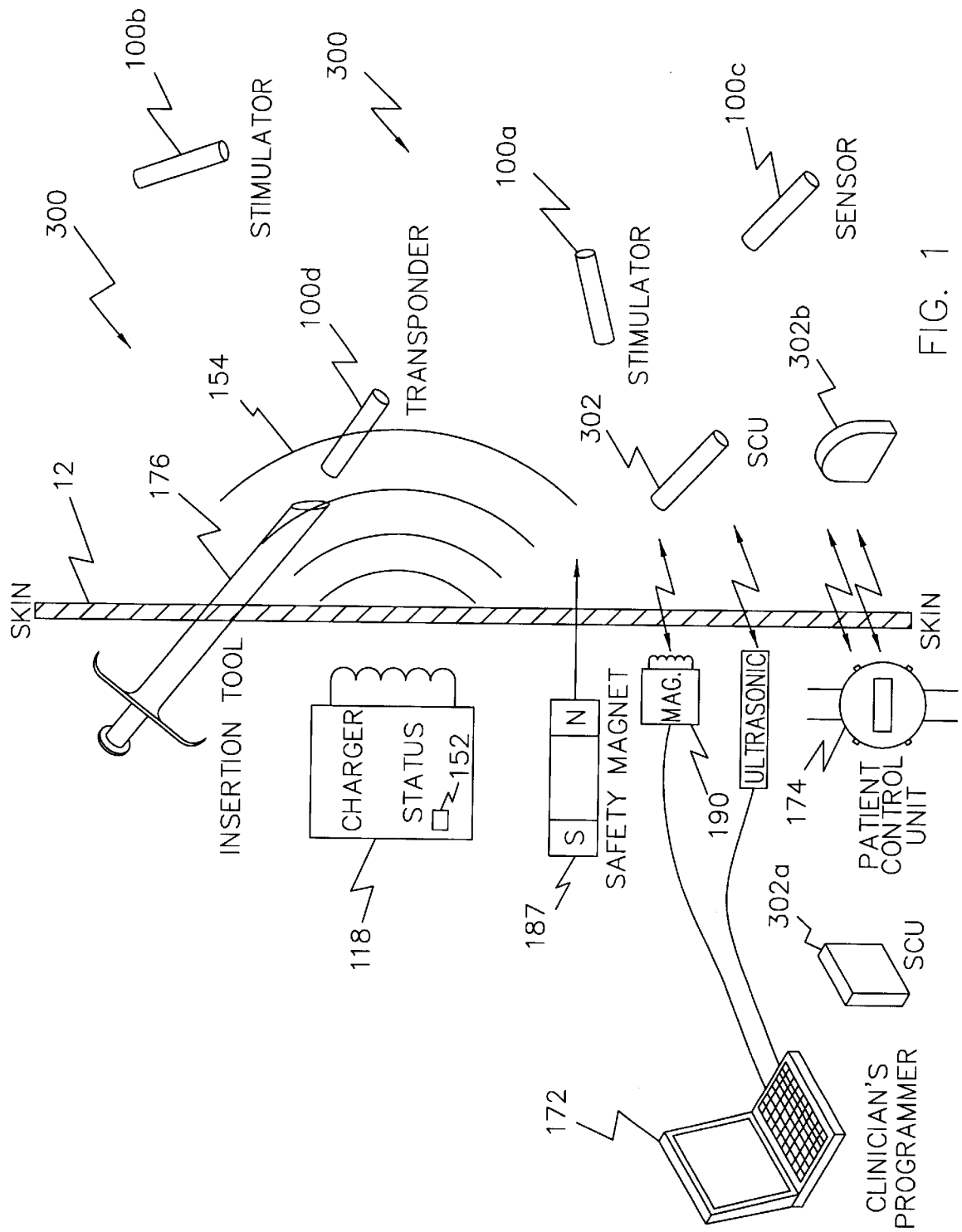
FIG. 1 is a simplified block diagram of an exemplary system suitable for practicing the communication protocol of the present invention, the system being comprised of implanted devices, e.g., microstimulators, microsensors and microtransponders, under control of an implanted system control unit (SCU).
Figure 2:
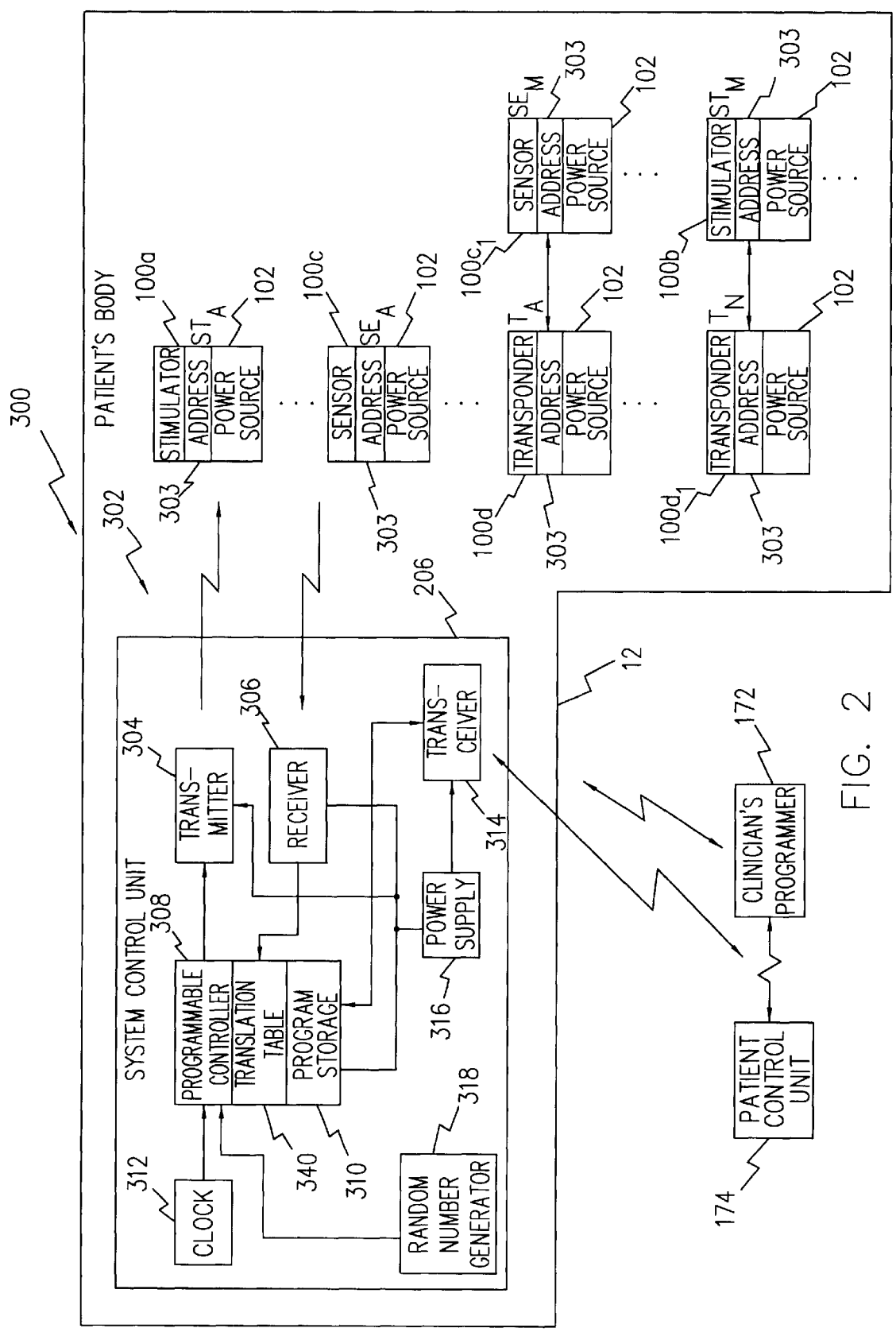
FIG. 2 comprises a block diagram of the system of FIG. 1 showing the functional elements that form the system control unit and implanted microstimulators, microsensors and microtransponders.

FIGS. 1 and 2 show an exemplary system 300 made of implanted devices 100, preferably battery powered, under control of a system control unit (SCU) 302, preferably also implanted beneath a patient's skin 12. As described in the '284 patent, potential implanted devices 100 (see also the block diagram shown in FIG. 3A) include stimulators, e.g., 100a and 100b, sensors, e.g., 100c, and transponders, e.g., 100d. The stimulators, e.g., 100a, can be remotely programmed to output a sequence of drive pulses to body tissue proximate to its implanted location via attached electrodes. The sensors, e.g., 100c, can be remotely programmed to sense one or more physiological or biological parameters in the implanted environment of the device, e.g., temperature, glucose level, $O_2$ content, nerve potential, muscle potential, etc. Transponders, e.g., 100d, are devices which can be used to extend the interbody communication range between stimulators and sensors and other devices, e.g., a clinician's programmer 172 and the patient control unit 174. Preferably, these stimulators, sensors and transponders are contained in sealed elongate housings having an axial dimension of less than 60 mm and a lateral dimension of less than 6 mm. Accordingly, such stimulators, sensors and transponders are respectively referred to as microstimulators, microsensors, and microtransponders or referred to in general as battery-powered, implantable stimulator/sensor devices. Such microstimulators and microsensors can thus be positioned beneath the skin 12 within a patient's body using a hypodermic type insertion tool 176.

As described in the '284 patent, microstimulators and microsensors are remotely programmed and interrogated via a wireless communication channel, e.g., modulated AC magnetic, sound (i.e., ultrasonic), RF or electric fields, typically originating from control devices external to the patient's body, e.g., the clinician's programmer 172 or patient control unit 174. Typically, the clinician's programmer 172 is used to program a single continuous or one time pulse sequence into each microstimulator and/or measure a biological parameter from one or more microsensors. Similarly, the patient control unit 174 typically communicates with the implanted devices 100, e.g., microsensors 100c, to monitor biological parameters. In order to distinguish each implanted device over the communication channel, each implanted device is manufactured with an address or identification code (ID) 303 specified in address storage circuitry 108 (see FIG. 3A) as described in the '284 patent.

By using one or more such implantable devices in conjunction with the SCU 302 of the present invention, the capabilities of such implanted devices can be further expanded. For example, in an open loop mode (described below in reference to FIG. 4), the SCU 302 can be programmed to periodically initiate tasks, e.g., perform real time tasking, such as transmitting commands to microstimulators according to a prescribed treatment regimen or periodically monitor biological parameters to determine a patient's status or the effectiveness of a treatment regimen. Alternatively, in a closed loop mode (described below in reference to FIGS. 5–7), the SCU 302 periodically interrogates one or more microsensors and accordingly adjust the commands transmitted to one or more microstimulators.

FIG. 2 shows a system 300 comprised of (1) one or more implantable devices 100 operable to sense and/or stimulate a patient's body parameter in accordance with one or more controllable operating parameters and (2) the SCU 302. The SCU 302 is primarily comprised of (1) a housing 206, preferably sealed and configured for implantation beneath the skin of the patient's body as described in the '284 patent in reference to the implanted devices 100, (2) a signal transmitter 304 in the housing 206 for transmitting command signals, (3) a signal receiver 306 in the housing 206 for receiving status signals, and (4) a programmable controller 308, e.g., a microcontroller or state machine, in the housing 206 responsive to received status signals for producing command signals for transmission by the signal transmitter 304 to other implantable devices 100. The sequence of operations of the programmable controller 308 is determined by an instruction list, i.e., a program, stored in program storage 310, coupled to the programmable controller 308. While the program storage 310 can be a nonvolatile memory device, e.g., ROM, manufactured with a program corresponding to a prescribed treatment regimen, it is preferable that at least a portion of the program storage 310 be an alterable form of memory, e.g., RAM, EEPROM, etc., whose contents can be remotely altered as described further below. However, it is additionally preferable that a portion of the program storage 310 be nonvolatile so that a default program is always present. The rate at which the program contained within the program storage 310 is executed is determined by clock/oscillator 312. Additionally, a real time clock operating in response to clock/oscillator 312 preferably permits tasks to be scheduled at specified times of day.

The signal transmitter 304 and signal receiver 306 preferably communicate with implanted devices 100 using an RF signal, e.g., a propagated electromagnetic wave, modulated by a command data signal. Alternatively, an audio transducer may be used to generate mechanical vibrations having a carrier frequency modulated by a command data signal. In an exemplary embodiment, a carrier frequency of 100 kHz is used which corresponds to a frequency that freely passes through a typical body's fluids and tissues. However, such sound means that operate at any frequency, e.g., greater than 1 Hz, are also considered to be within the scope of the present invention. Alternatively, the signal transmitter 304 and signal receiver 306 can communicate using modulated AC, e.g., magnetic fields.

The clinician's programmer 172 and/or the patient control unit 174 and/or other external control devices can also communicate with the implanted devices 100, as described in the '284 patent, preferably using a modulated RF or AC magnetic field. Alternatively, such external devices can communicate with the SCU 302 via a transceiver 314 coupled to the programmable controller 308. Since, the signal transmitter 304 and signal receiver 306 may operate using a different communication means, a separate transceiver 314 which operates using an alternative communication means may be used for communicating with external devices. However, a single transmitter 304/receiver 306 can be used in place of transceiver 314 for communicating with the external devices and implanted devices if a common communication means is used.

Figure 3A:
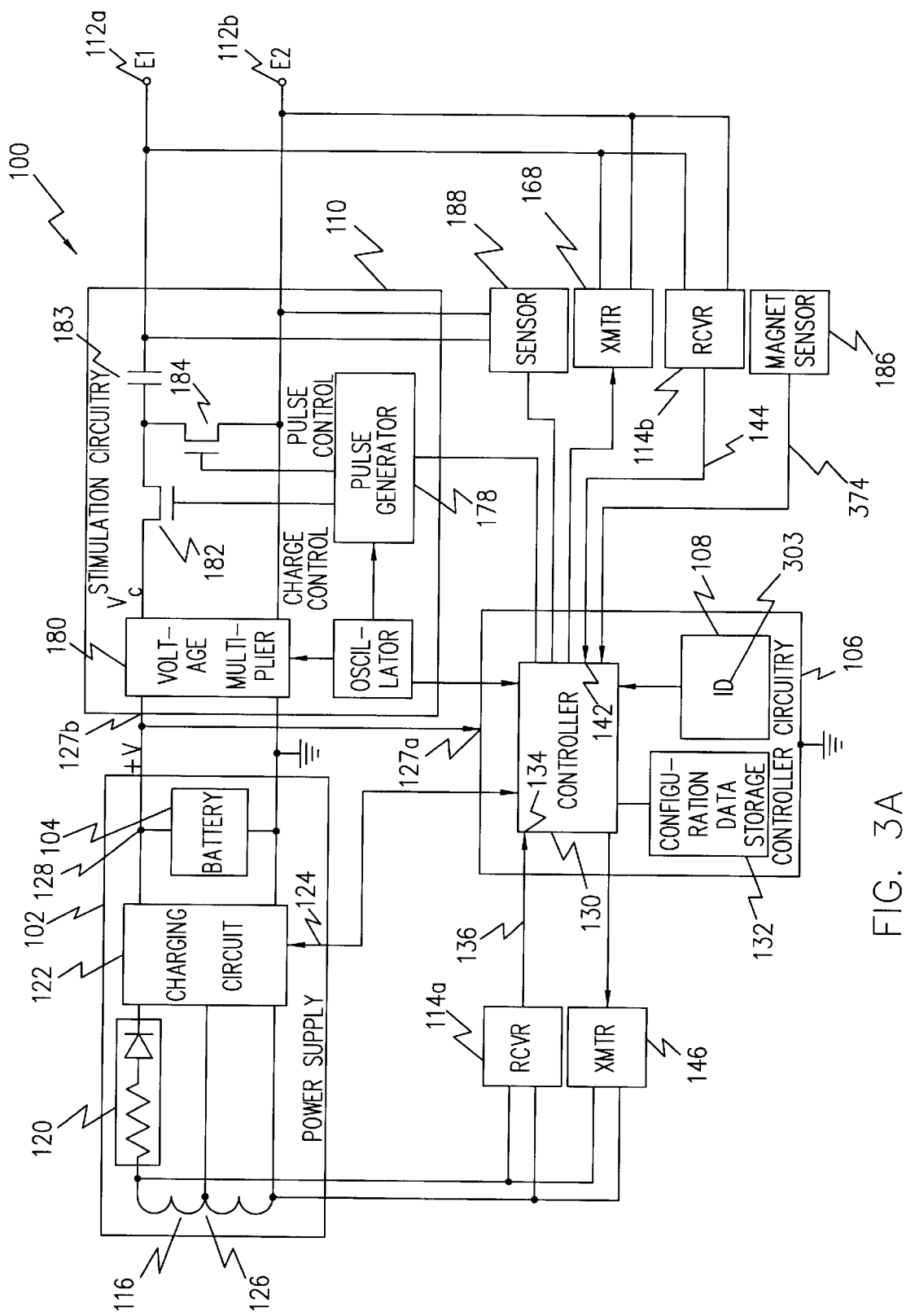
FIG. 3A comprises a block diagram of an exemplary implantable device, as shown in U.S. Pat. No. 6,164,284, including a battery for powering the device for a period of time in excess of one hour in response to a command from the system control unit.
Figure 3B:
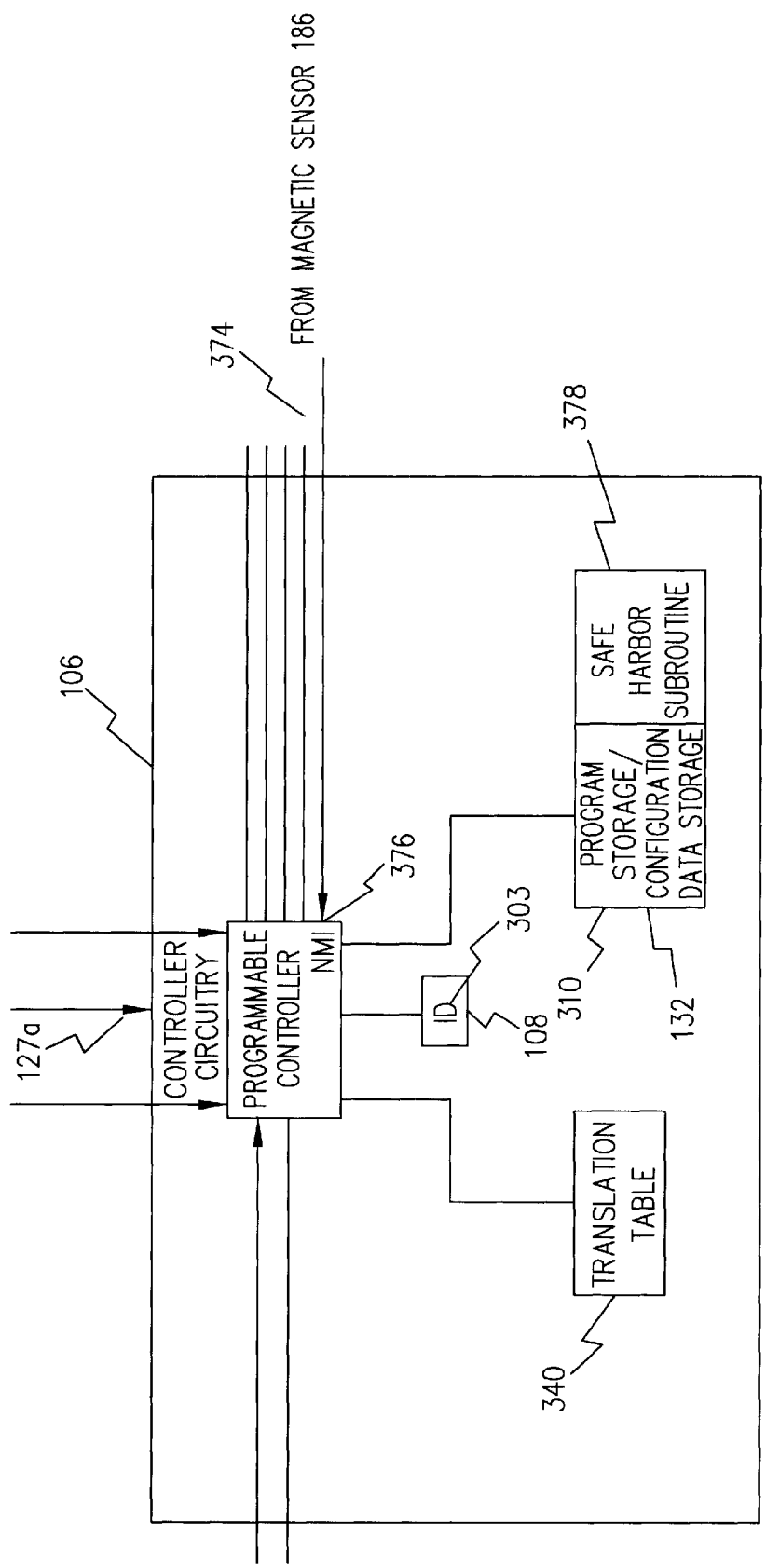
FIG. 3B comprises a simplified block diagram of controller circuitry that can be substituted for the controller circuitry of FIG. 3A, thus permitting a single device to be configured as a system control unit and/or a microstimulator and/or a microsensor and/or a microtransponder.

FIG. 3A comprises a block diagram of an exemplary implantable device 100 operable under control of controller circuitry 106 and includes a battery 104, preferably rechargeable, for powering the device for a period of time in excess of one hour and responsive to command signals from a remote device, e.g., the SCU 302. The controller circuitry 106 is primarily comprised of a controller 130, configuration data storage 132 for prescribing its operation, and address storage circuitry 108 for storing the ID 303 of the device. As described in the '284 patent, the implantable device 100 is preferably configurable to alternatively operate as a microstimulator and/or microsensor and/or microtransponder due to the commonality of most of the circuitry contained within. Such circuitry may be further expanded to permit a common block of circuitry to also perform the functions required for the SCU 302. Accordingly, FIG. 3B shows an alternative implementation of the controller circuitry 106 of FIG. 3A that is suitable for implementing a microstimulator and/or a microsensor and/or a microtransponder and/or the SCU 302. In this implementation, the configuration data storage 132 can be alternatively used as the program storage 310 when the implantable device 100 is used as the SCU 302. In this implementation, XMTR 168 corresponds to the signal transmitter 304 and the RCVR 114b corresponds to the signal receiver 306 (preferably operable via electrodes 112a and 112b operating as an RF antenna) and the RCVR 114a and XMTR 146 correspond to the transceiver 314 (preferably operable via coil 116 for AC magnetic modes of communication).

In a preferred embodiment, the contents of the program storage 310, i.e., the software that controls the operation of the programmable controller 308, can be remotely downloaded, e.g., from the clinician's programmer 172 using data modulated onto an RF signal or an AC magnetic field. In this embodiment, it is preferable that the contents of the program storage 310 for each SCU 302 be protected from an inadvertent change. Accordingly, the contents of the address storage circuitry 108, i.e., the ID 303, is preferably used as a security code to confirm that the new program storage contents are destined for the SCU 302 receiving the data. This feature is significant if multiple patient's could be physically located, e.g., in adjoining beds, within the communication range of the clinician's programmer 172.

In a further aspect of the present invention, it is preferable that the SCU 302 be operable for an extended period of time, e.g., in excess of one hour, from an internal power supply 316 (see FIG. 2). While a primary battery, i.e., a nonrechargeable battery, is suitable for this function, it is preferable that the power supply 316 include a rechargeable battery, e.g., battery 104 as described in the '284 patent, that can be recharged via an AC magnetic field produced external to the patient's body. Accordingly, power supply 102 of FIG. 3A is the preferred power supply 316 for the SCU 302 as well.

The battery-powered devices 100 of the '284 patent are preferably configurable to operate in a plurality of operational modes, e.g., via a communicated command signal. In a first operational mode, device 100 is remotely configured to be a microstimulator, e.g., 100a and 100b. In this embodiment (see FIG. 3A), controller 130 commands stimulation circuitry 110 to generate a sequence of drive pulses through electrodes 112 to stimulate tissue, e.g., a nerve or muscle, proximate to the implanted location of the microstimulator, e.g., 100a or 100b. In operation, a programmable pulse generator 178 and voltage multiplier 180 are configured with parameters corresponding to a desired pulse sequence and specifying how much to multiply (or divide) the battery voltage (e.g., by summing charged capacitors or similarly charged battery portions) to generate a desired compliance voltage $V_c$. A first FET 182 is periodically energized to store charge into capacitor 183 (in a first direction at a low current flow rate through the body tissue) and a second FET 184 is periodically energized to discharge capacitor 183 in an opposing direction at a higher current flow rate which stimulates a nearby muscle or nerve. Alternatively, electrodes can be selected that will form an equivalent capacitor within the body tissue.

In a next operational mode, the battery-powered implantable device 100 can be configured to operate as a microsensor, e.g., 100c, that can sense one or more physiological or biological parameters in the implanted environment of the device. In accordance with a preferred mode of operation, the system control unit 302 periodically requests the sensed data from each microsensor 100c using its ID 303 stored in the address storage circuitry 108, and responsively sends command signals to microstimulators, e.g., 100a and 100b, adjusted accordingly to the sensed data. For example, sensor circuitry 188 can be coupled to the electrodes 112 to sense or otherwise used to measure a biological parameter, e.g., temperature, glucose level, $O_2$ content, voltage, current, impedance, etc. and provide the sensed data to the controller circuitry 106. Preferably, the sensor circuitry 188 includes a programmable bandpass filter and an analog to digital (A/D) converter that can sense and accordingly convert the voltage levels across the electrodes 112 into a digital quantity. Alternatively, the sensor circuitry 188 can include one or more sense amplifiers to determine if the measured voltage exceeds a threshold voltage value or is within a specified voltage range. Furthermore, the sensor circuitry 188 can be configurable to include integration circuitry to further process the sensed voltage. The operational mode of the voltage sensor circuitry 188 is remotely programmable via the device's communication interface.

Additionally, the sensing capabilities of a microsensor preferably include the capability to monitor the battery status via path 124 from the charging circuit 122 and can additionally include using an ultrasonic transducer (not shown) or the coil 116 to respectively measure the ultrasonic, magnetic or propagated RF signal magnitudes (or communication time delays) of signals transmitted between a pair of implanted devices and thus determine the relative locations of these devices. This information can be used to determine the amount of body movement, e.g., the amount that an elbow or finger is bent, and thus form a portion of a closed loop motion control system.

In another operational mode, the battery-powered implantable device 100 can be configured to operate as a microtransponder, e.g., 100d. In this operational mode, the microtransponder receives (via the aforementioned RCVR 114a using AC magnetic, sonic, RF, or electric communication modes) a first command signal from the SCU 302 and retransmits this signal (preferably after reformatting) to other implanted devices (e.g., microstimulators, microsensors, and/or microtransponders) using the aforementioned XMTR 168 using magnetic, sonic, RF or electric communication modes. While a microtransponder may receive one mode of command signal, e.g., magnetic, it may retransmit the signal in another mode, e.g., RF. For example, clinician's programmer 172 may emit a modulated magnetic signal using a magnetic emitter 190 (see FIG. 1) to program/ command the implanted devices 100. However, the magnitude of the emitted signal may not be sufficient to be successfully received by all of the implanted devices 100. As such, a microtransponder 100d may receive the modulated magnetic signal and retransmit it (preferably after reformatting) as a modulated ultrasonic or RF signal which can pass through the body with fewer restrictions. In another exemplary use, the patient control unit 174 may need to monitor a microsensor 100c in a patient's foot. Despite the efficiency of ultrasonic, magnetic and propagated RF communication in a patient's body, such a signal could still be insufficient to pass from a patient's foot to a patient's wrist (the typical location of the patient control unit 174). As such, a microtransponder 100d could be implanted (if needed) in the patient's torso to improve the communication link.

Figure 4:
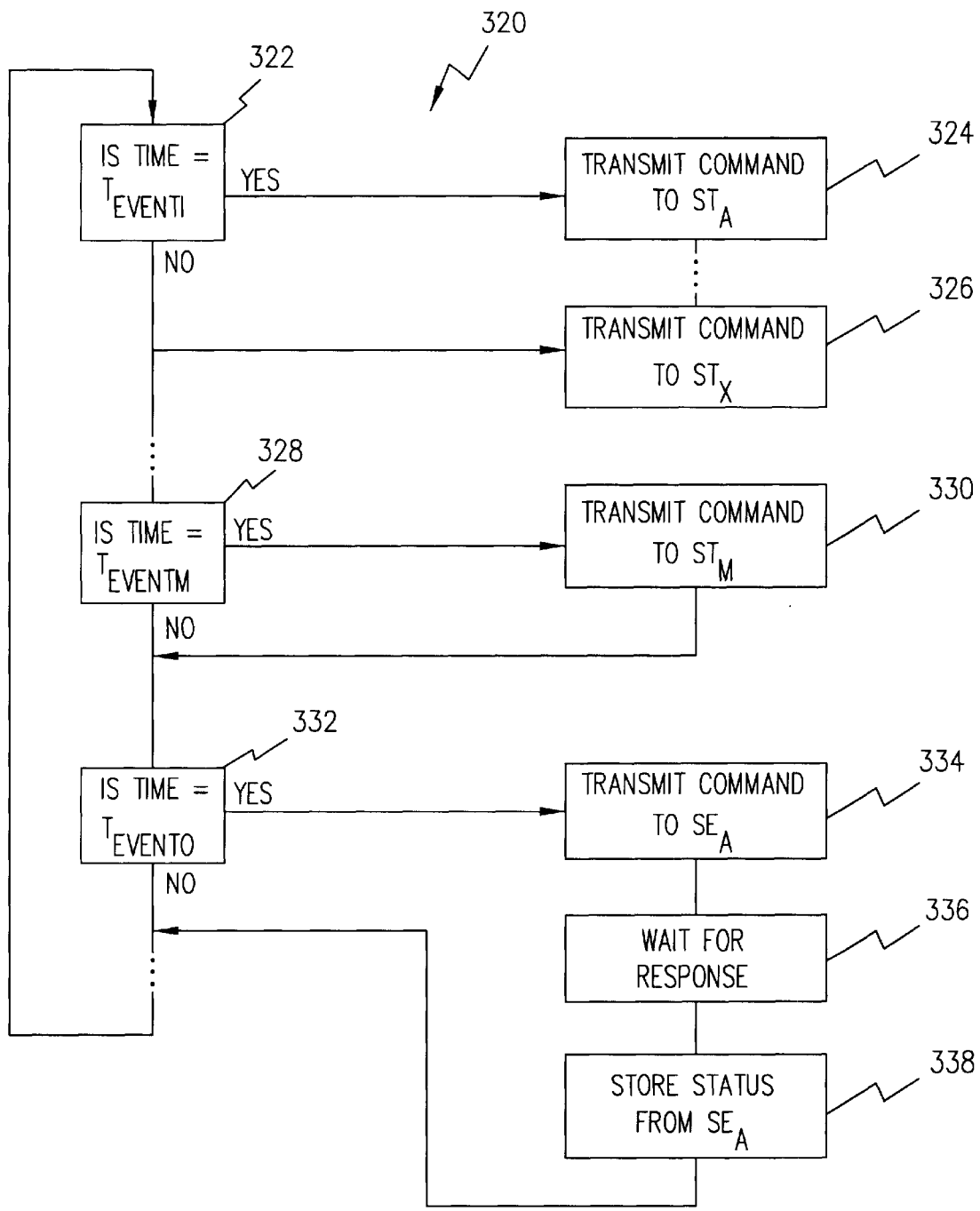
FIG. 4 shows an exemplary flow chart of the use of the exemplary system in an open loop mode for controlling/monitoring a plurality of implanted devices, e.g., microstimulators, microsensors.

FIG. 4 shows a block diagram of an exemplary open loop control program, i.e., a task scheduler 320, for controlling/ monitoring a body function/parameter. In this process, the programmable controller 308 is responsive to the clock 312 (preferably a crystal controlled oscillator to thus permit real time scheduling) in determining when to perform any of a plurality of tasks. In this exemplary flow chart, the programmable controller 308 first determines in block 322 if it is now at a time designated as $T_{EVENT1}$ (or at least within a sampling error of that time), e.g., at 1:00 AM. If so, the programmable controller 308 transmits a designated command to microstimulator A ($ST_A$) in block 324. In this example, the control program continues where commands are sent to a plurality of stimulators and concludes in block 326 where a designated command is sent to microstimulator X ($ST_X$). Such a subprocess, e.g., a subroutine, is typically used when multiple portions of body tissue require stimulation, e.g., stimulating a plurality of muscle groups in a paralyzed limb to avoid atrophy. The task scheduler 320 continues through multiple time event detection blocks until in block 328 it determines whether the time $T_{EVENTM}$ has arrived. If so, the process continues at block 330 where, in this case, a single command is sent to microstimulator M (ST$_M$). Similarly, in block 332 the task scheduler 320 determines when it is the scheduled time, i.e., T$_{EVENT0}$, to execute a status request from microsensor A (SE$_A$). If so, a subprocess, e.g., a subroutine, commences at block 334 where a command is sent to microsensor A (SE$_A$) to request sensor data and/or specify sensing criteria. Microsensor A (SE$_A$) does not instantaneously respond. Accordingly, the programmable controller 308 waits for a response in block 336. In block 338, the returned sensor status data from microsensor A (SE$_A$) is stored in a portion of the memory, e.g., a volatile portion of the program storage 310, of the programmable controller 308. The task scheduler 320 can be a programmed sequence, i.e., defined in software stored in the program storage 310, or, alternatively, a predefined function controlled by a table of parameters similarly stored in the program storage 310. A similar process may be used where the SCU 302 periodically interrogates each implantable device 100 to determine its battery status.

Figure 5:
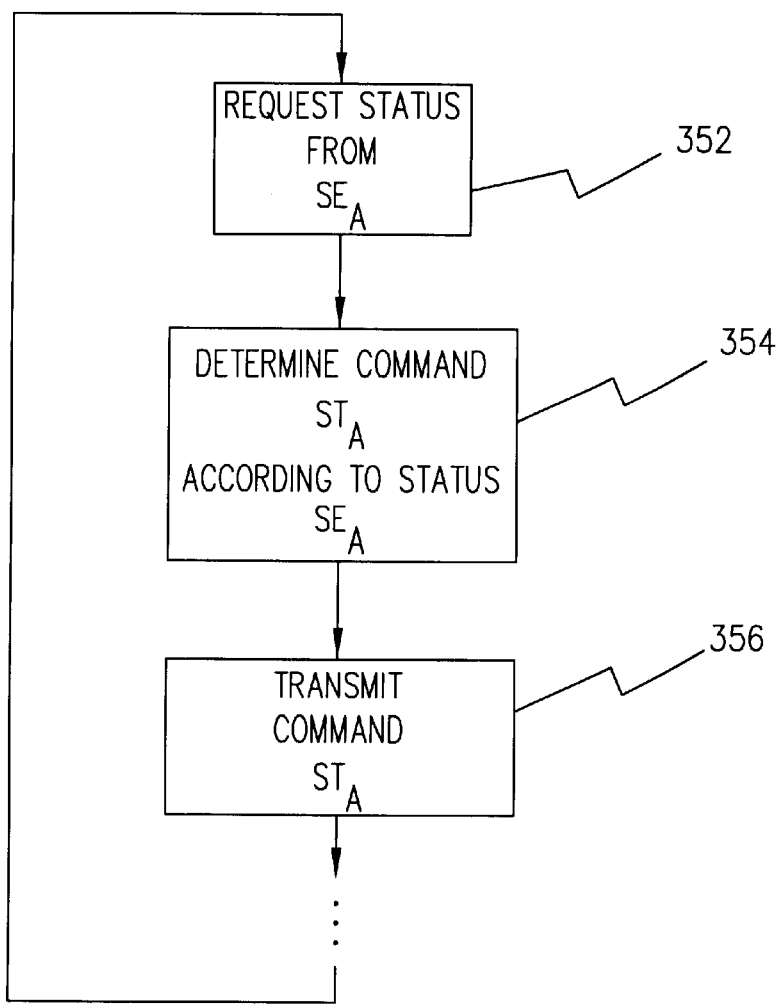
FIG. 5 shows a simplified flow chart of the use of closed loop control of a microstimulator by altering commands from the system control unit in response to status data received from a microsensor.

FIG. 5 is an exemplary block diagram showing the use of the system of the present invention to perform closed loop control of a body function. In block 352, the SCU 302 requests status from microsensor A (SE$_A$). The SCU 302, in block 354, then determines whether the present command given to a microstimulator is satisfactory and, if necessary, determines a new command and transmits the new command to the microstimulator A (ST$_A$) in block 356. For example, if microsensor A (SE$_A$) is reading a voltage corresponding to the degree of contraction resulting from stimulating a muscle, the SCU 302 could transmit a command to microstimulator A (ST$_A$) to adjust the sequence of drive pulses, e.g., in magnitude, duty cycle, etc., and accordingly change the voltage sensed by microsensor A (SE$_A$). Accordingly, closed loop, i.e., feedback, control is accomplished. The characteristics of the feedback (position, integral, derivative (PID)) control are preferably program controlled by the SCU 302 according to the control program contained in program storage 310.

Figure 6:
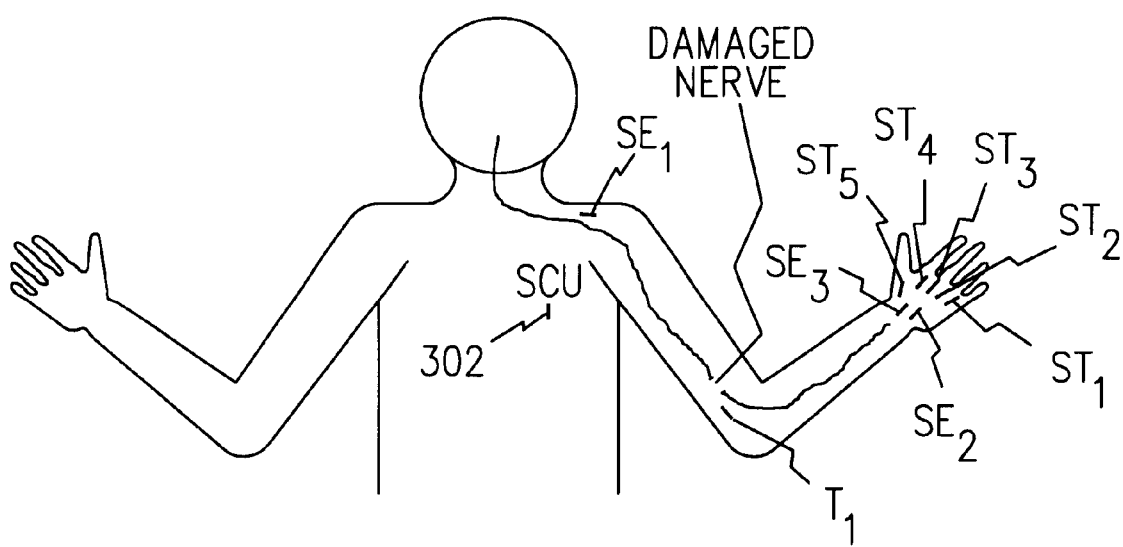
FIG. 6 shows an exemplary injury, i.e., a damaged nerve, and the placement of a plurality of implanted devices, i.e., microstimulators, microsensors and a microtransponder under control of the system control unit for "replacing" the damaged nerve.

FIG. 6 shows an exemplary injury treatable by embodiments of the present system 300. In this exemplary injury, the neural pathway has been damaged, e.g., severed, just above the a patient's left elbow. The goal of this exemplary system is to bypass the damaged neural pathway to permit the patient to regain control of the left hand. An SCU 302 is implanted within the patient's torso to control a plurality of stimulators, ST$_1$–ST$_5$, implanted proximate to the muscles respectively controlling the patient's thumb and fingers (shown in the patient's hand for simplicity). Additionally, microsensor 1 (SE$_1$) is implanted proximate to an undamaged nerve portion where it can sense a signal generated from the patient's brain when the patient wants hand closure. Optional microsensor 2 (SE$_2$) is implanted in a portion of the patient's hand where it can sense a signal corresponding to stimulation/motion of the patient's pinky finger and microsensor 3 (SE$_3$) is implanted and configured to measure a signal corresponding to grip pressure generated when the fingers of the patient's hand are closed. Additionally, an optional microtransponder (T$_1$) is shown which can be used to improve the communication between the SCU 302 and the implanted devices.

Figure 7:
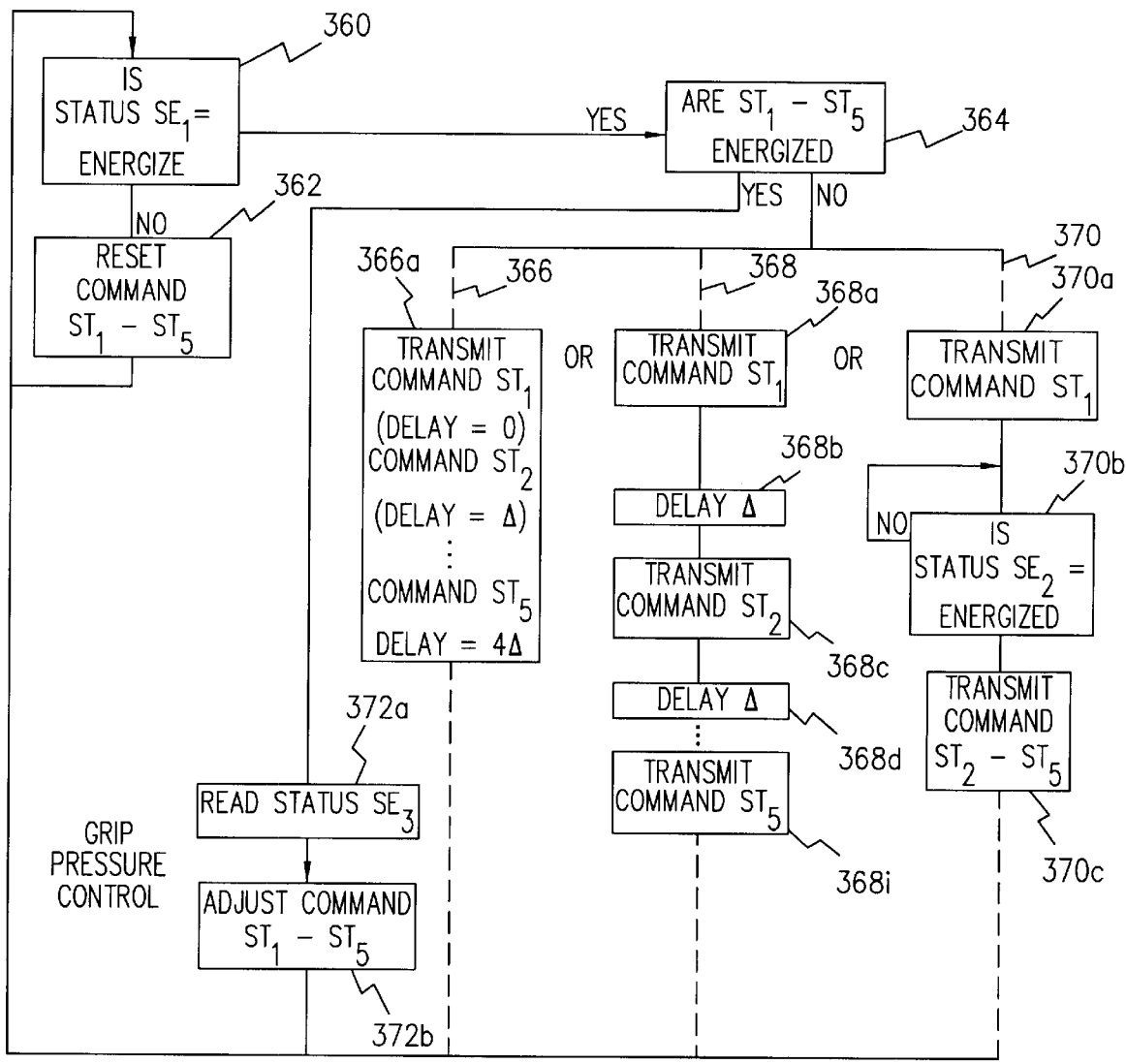
FIG. 7 shows a simplified flow chart of the control of the implanted devices of FIG. 6 by the system control unit.

FIG. 7 shows an exemplary flow chart for the operation of the SCU 302 in association with the implanted devices in the exemplary system of FIG. 6. In block 360, the SCU 302 interrogates microsensor 1 (SE$_1$) to determine if the patient is requesting actuation of his fingers. If not, a command is transmitted in block 362 to all of the stimulators (ST$_1$–ST$_5$) to open the patient's hand, i.e., to de-energize the muscles which close the patient's fingers. If microsensor 1 (SE$_1$) senses a signal to actuate the patient's fingers, the SCU 302 determines in block 364 whether the stimulators ST$_1$–ST$_5$ are currently energized, i.e., generating a sequence of drive/stimulation pulses. If not, the SCU 302 executes instructions to energize the stimulators. In a first optional path 366, each of the stimulators is simultaneously (subject to formatting and transmission delays) commanded to energize in block 366a. However, the command signal given to each one specifies a different start delay time. Accordingly, there is a stagger between the actuation/closing of each finger.

In a second optional path 368, the microstimulators are consecutively energized by a delay Δ. Thus, microstimulator 1 (ST$_1$) is energized in block 368a, a delay is executed within the SCU 302 in block 368b, and so on for all of the microstimulators. Accordingly, paths 366 and 368 perform essentially the same function. However, in path 366 the interdevice timing is performed by the clocks within each implanted device 100 while in path 368, the SCU 302 is responsible for providing the interdevice timing.

In path 370, the SCU 302 actuates a first microstimulator (ST$_1$) in block 370a and waits in block 370b for its corresponding muscle to be actuated, as determined by microsensor 2 (SE$_2$), before actuating the remaining stimulators (ST$_2$–ST$_5$) in block 370c. This implementation could provide more coordinated movement in some situations.

Once the stimulators have been energized, as determined in block 364, closed loop grip pressure control is performed in blocks 372a and 372b by periodically reading the status of microsensor 3 (SE$_3$) and adjusting the commands given to the stimulators (ST$_1$–ST$_5$) accordingly. Consequently, this exemplary system has enabled the patient to regain control of his hand including coordinated motion and grip pressure control of the patient's fingers.

Referring again to FIG. 3A, a magnetic sensor 186 is shown. In the '284 patent, it was shown that such a sensor 186 could be used to disable the operation of an implanted device 100, e.g., to stop or otherwise alter the operation of such devices in an emergency situation, in response to a DC magnetic field, preferably from an externally positioned safety magnet 187 (see FIG. 1). Additionally, it is noted that power to at least some portions of a preferred implantable device may be removed when a magnetic field is sensed and thus power may be conserved. The magnetic sensor 186 can be implemented using various devices. Exemplary of such devices are devices manufactured by Nonvolatile Electronics, Inc. (e.g., their AA, AB, AC, AD, or AG series), Hall effect sensors, magnetoresistive sensors, and subminiature reed switches. Such miniature devices are configurable to be placed within the housing of the SCU 302 and implantable devices 100. While essentially passive magnetic sensors, e.g., reed switches, are possible, the remaining devices may include active circuitry that consumes power during detection of the DC magnetic field. Accordingly, it is preferred that controller circuitry 302 periodically, e.g., once a second, provide power to the magnetic sensor 186 and sample the magnetic sensor's output signal 374 during that sampling period. Additionally, a magnetoresistive sensor is especially preferred due to its small size that enables its use within the preferred implantable device 100 while conserving the available internal package volume.

Figure 8:
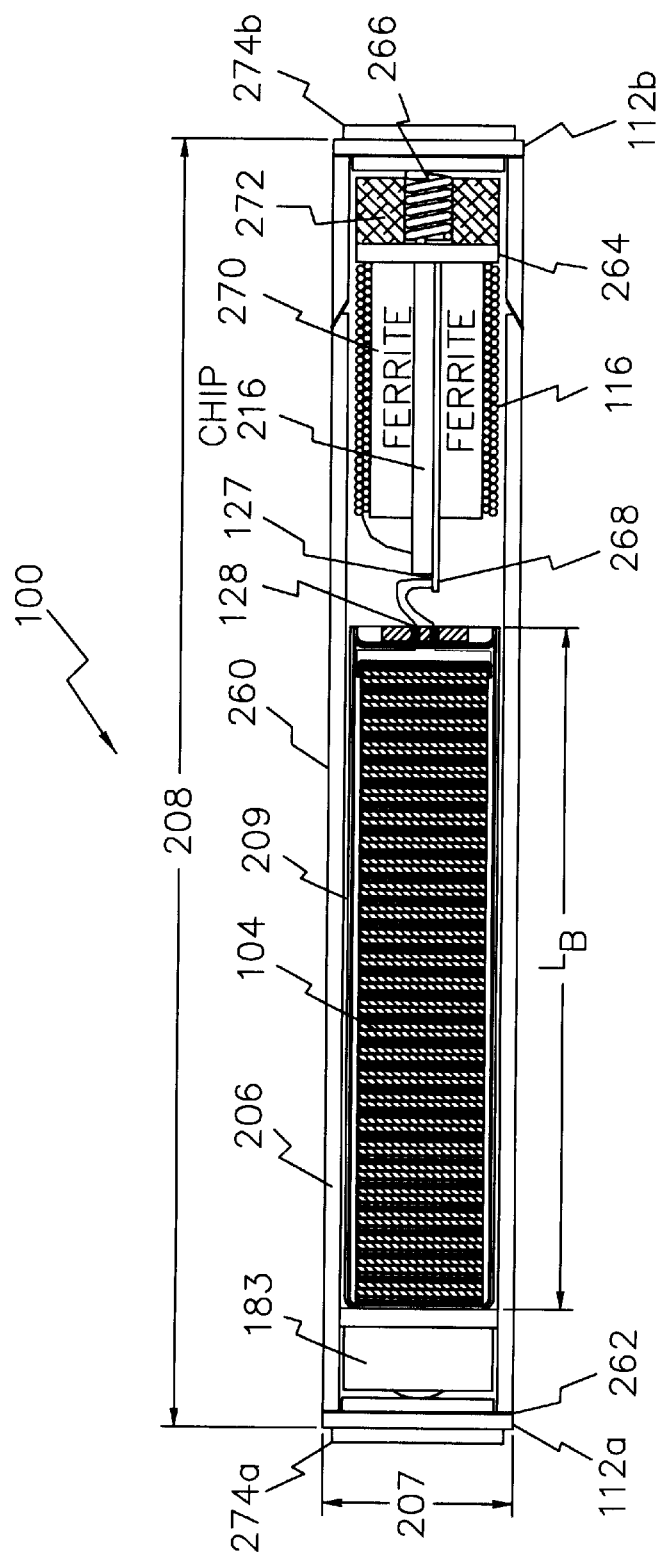
FIG. 8 shows a side cutaway view of an exemplary implantable ceramic tube suitable for the housing the system control unit and/or microstimulators and/or microsensors and/or microtransponders.

FIG. 8 shows a side cutaway view of an exemplary sealed housing 206 (described in detail in the '284 patent which is incorporated herein by reference), the battery 104 and the circuitry (implemented on one or more IC chips 216 to implement electronic portions of the SCU 302 or implantable device 100) contained within. In this exemplary construction, the housing 206 is comprised of an insulating ceramic tube 260 having electrodes 112a and 112b on opposing ends. The circuitry within primarily comprises the capacitor 183 (used when in a microstimulator mode), battery 104, and IC chips 216. Additionally, a platinum, iridium, or platinum-iridium disks or plates 274a and 274b are preferably welded to the end caps 112a, 112b to minimize the impedance of the connection to the body tissue.

The battery 104 used for powering the implantable device 100 (or SCU 302) is made from appropriate materials so as to preferably provide a power capacity of at least 1 microwatt-hour. Preferably, such a battery, e.g., a Li—I battery, has an energy density of about 240 mw-Hr/cm$^3$. The battery voltage V of an exemplary battery is nominally 3.6 volts, which is more than adequate for operating the CMOS circuits preferably used to implement the IC chip(s) 216, and/or other electronic circuitry, within the SCU 302.

The battery 104 may take many forms, any of which may be used so long as the battery can be made to fit within the small volume available. The battery 104 may be either a primary battery or a rechargeable battery. A primary battery offers the advantage of not requiring a recharging circuit and the disadvantage of not being rechargeable (which means once its energy has been used up, the implanted device no longer functions).

One of the more difficult hurdles facing the use of the battery 104 within the SCU 302 or implantable device 100 relates to the relatively small size or volume inside the housing 206 within which the battery must be inserted. A typical SCU 302 or implantable device 100 made in accordance with the present invention is no larger than about 60 mm long and 8 mm in diameter, preferably no larger than 60 mm long and 6 mm in diameter, and includes even smaller embodiments, e.g., 15 mm long with an O.D. of 2.2 mm (resulting in an I.D. of about 2 mm). When one considers that only about ¼ to ½ of the available volume within the device housing 206 is available for the battery, one begins to appreciate more fully how little volume, and thus how little battery storage capacity, is available for the SCU 302 or the implantable devices 100 and why it is desirable to minimize average power consumption to extend battery life.

A preferred system for practicing the present invention is comprised of an implanted SCU 302 and a plurality of implanted devices 100, each of which contains its own rechargeable battery 104. As such, a patient is essentially independent of any external apparatus between battery chargings (which generally occur no more often than once an hour and preferably no more often than once every 24 hours). However, for some treatment regimens, it may be adequate to use a power supply analogous to that described in U.S. Pat. No. 5,324,316 that only provides power while an external AC magnetic field is being provided, e.g., from charger 118. Additionally, it may be desired, e.g., from a cost or flexibility standpoint, to implement the SCU 302 as an external device, e.g., within a watch-shaped housing that can be attached to a patient's wrist in a similar manner to the patient control unit 174.

The power consumption of the SCU 302 is primarily dependent upon the circuitry implementation, preferably CMOS, the circuitry complexity and the clock speed. For a simple system, a CMOS implemented state machine will be sufficient to provide the required capabilities of the programmable controller 308. However, for more complex systems, e.g., a system where an SCU 302 controls a large number of implanted devices 100 in a closed loop manner, a microcontroller may be required. As the complexity of such microcontrollers increases (along with its transistor count), so does its power consumption. Accordingly, a larger battery having a capacity of 1 to 10 watt-hours is preferred. While a primary battery is possible, it is preferable that a rechargeable battery be used. Such larger batteries will require a larger volume and accordingly, cannot be placed in the injectable housing described above.

Since only one SCU is required to implement a system, the battery life of the SCU may be accommodated by increasing the casing size (e.g., increasing at least one dimension to be in excess of 1 inch) for the SCU to accommodate a larger sized battery and either locating the larger SCU 302a (see FIG. 1) external to patient's body or the single larger SCU 302b may be surgically implanted. However, the battery life of each of the microstimulators, microsensor, microtransponders (hereinafter referred to as battery-powered implantable stimulation/sensor devices) is much more significant since (1) it is desirable that these devices be small enough to be injectable and (2) an exemplary system will contain many more, e.g., between 10 to 1000, devices, so that it would be impractical to have more than a few larger-sized devices in a patient's body. Since increasing the battery size of the injectable implantable devices 100 is impractical, the present invention primarily addresses a method to increase the battery life of the injectable implantable devices 100 by decreasing their average power consumption. Accordingly, implantable devices practicing the present invention operate for extended periods of time, e.g., 24 hours or more, between rechargings.

Figure 14A:
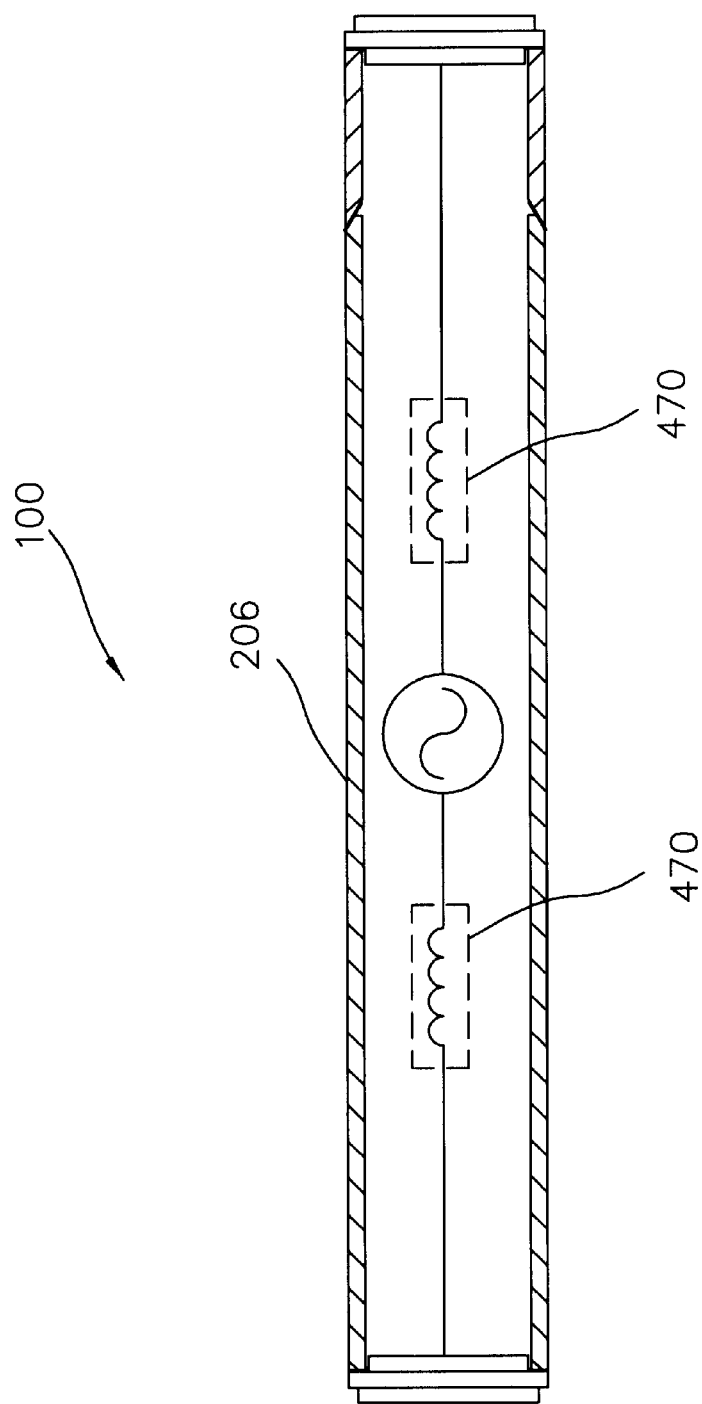
FIGS. 14A and 14B show exemplary implementations of antennas that may be used with embodiments of the present invention.
Figure 14B:
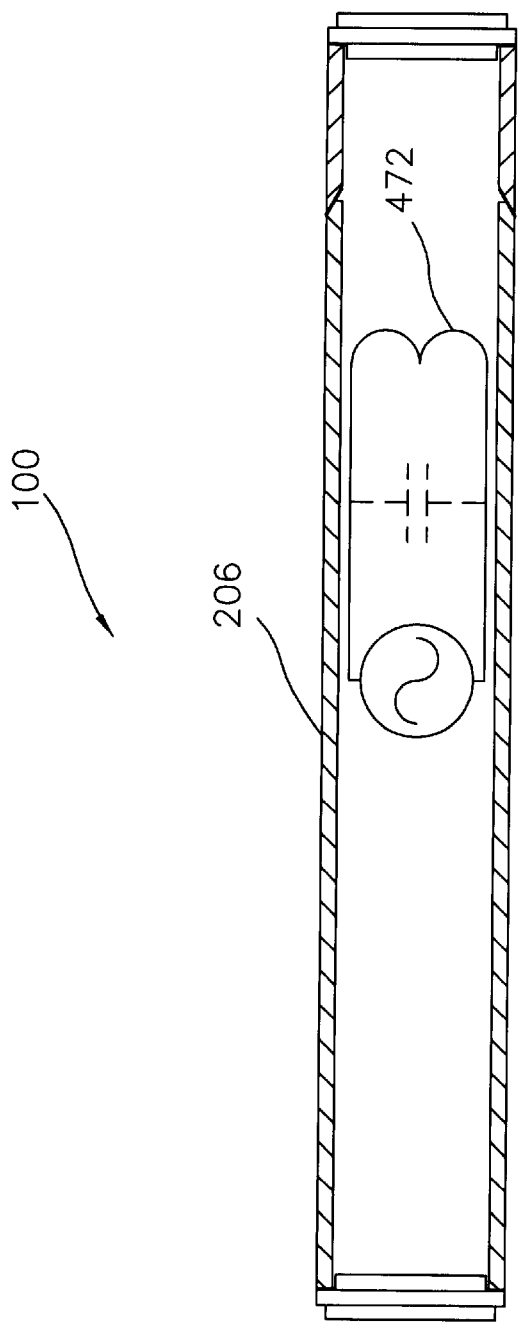

A radio frequency propagated transmitter may be hooked up to one or both of the electrodes forming a dipole antenna that can be tuned with balun coil(s) 470 (optional) to radiate (see FIG. 14A). A coil 472 inside the ceramic case (and its associated parasitic capacitance) would also work as an RF antenna (see FIG. 14B). Depending on the frequency, antenna noise level, and receiver sensitivity, a power between 0.1 mw (milliwatts) and 20 mw would radiate adequately to communicate with a SCU about five feet away.

Figure 9:
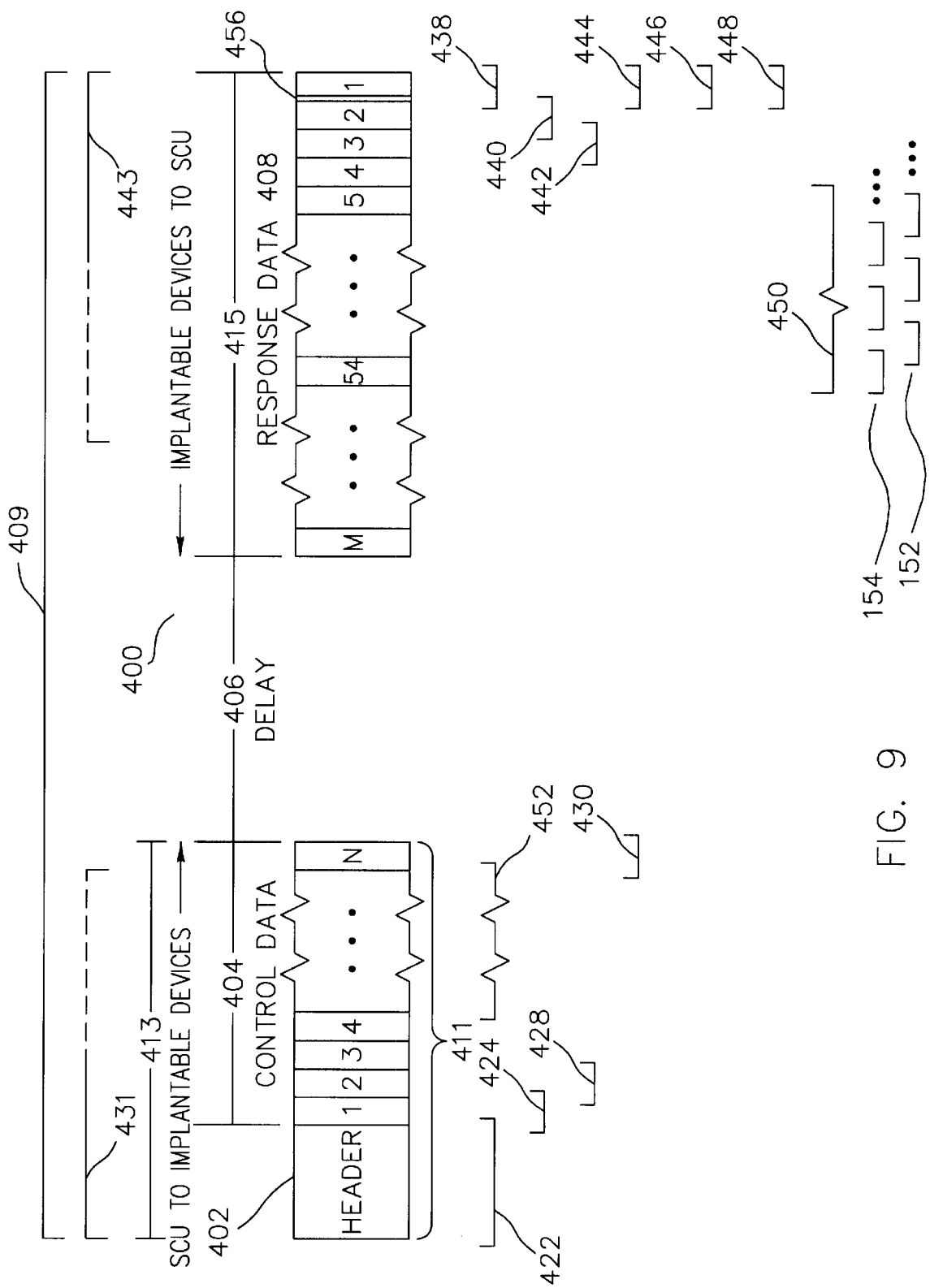
FIG. 9 is a simplified diagram of a communication protocol configured to extend the battery life of an implantable device.
Figure 10:
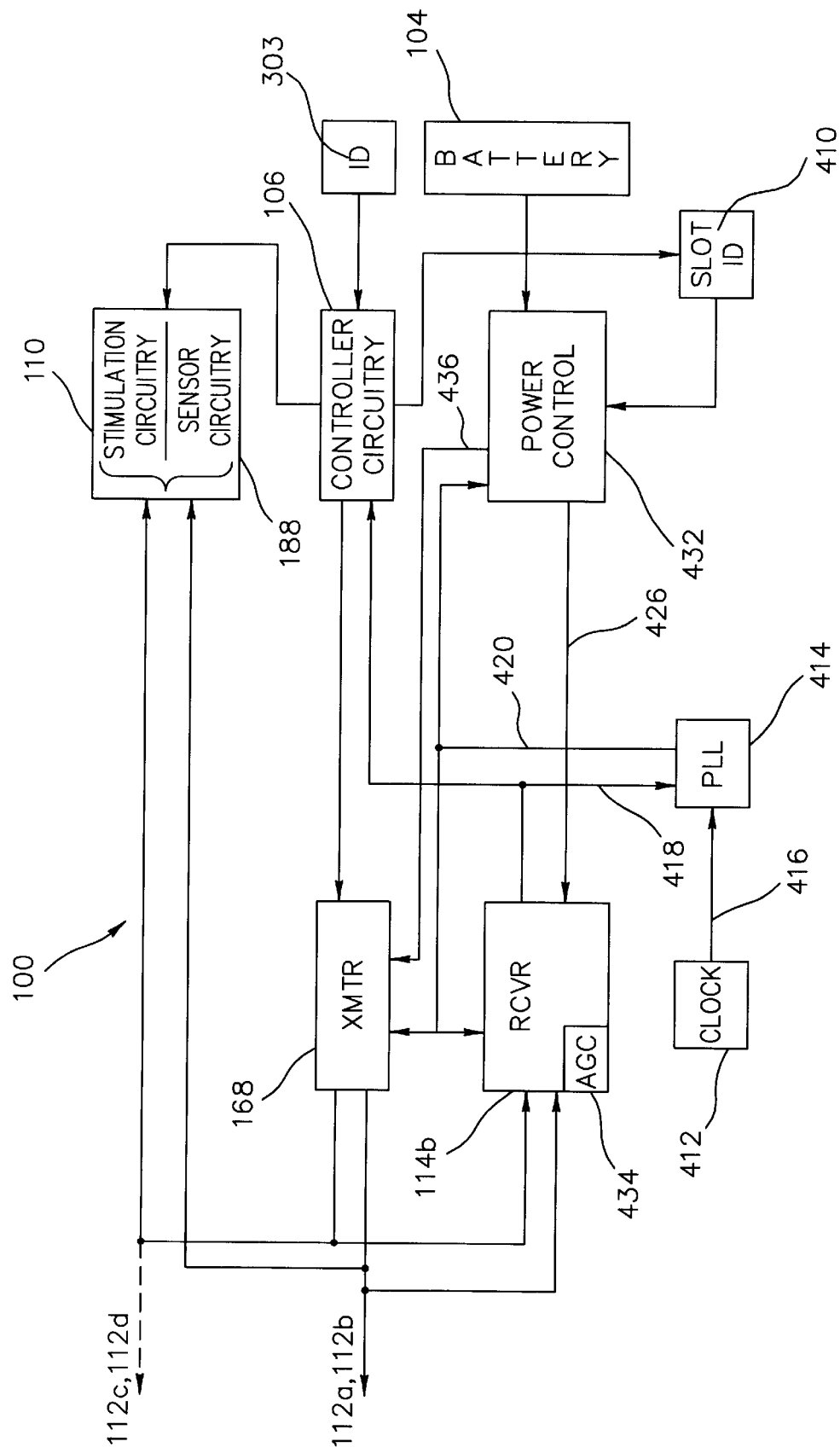
FIG. 10 is a simplified block diagram of an implantable device, such as that shown in FIG. 3A, that is particularly directed to the power consumption features facilitated by the communication protocol of FIG. 9.

FIG. 9 shows a simplified diagram of a communication protocol for communicating between the SCU 302 (see, e.g., FIG. 2) and a plurality of implantable devices 100 that is configured to facilitate decreasing the average power consumption of the implantable devices 100 (a block diagram of a single implantable device 100 is shown in FIG. 10 which is a simplified block diagram of much of what has already been shown in FIG. 3A). Each implantable device 100 consumes a base amount of power since many of the components of the implantable device 100 consume power a majority of the time, e.g., much of the circuitry associated with the controller circuitry 106 may always be powered. The power consumption of such portions may be decreased by using CMOS or similar implementations. Other portions of the circuitry only need to consume power at specific times during the operation of the device. For example, much of the stimulation circuitry 110 only needs to consume power when a tissue stimulation signal is emitted, which may be at a relatively low duty cycle. Similarly, the sensor circuitry 188 may also be used at a relatively low duty cycle, e.g., as low as 0% for an implantable device 100 that only functions as a microstimulator. The present invention extends this philosophy of only powering necessary circuitry during their operational time periods to a communication protocol suitable for extending the battery life of such implantable devices.

For implementing the communication protocol, each implantable device 100 uses the controller circuitry 106 which controls the operation of the implantable device 100 (as well as the implantable device's side of the communication protocol) and transfers data to and from the XMTR 168 and the RCVR 114b (which communicate with the SCU 302), each of which drains a significant amount of current and thus power from the battery 104 (relative to the limited battery capacity dictated by the physical package size of the implantable device 100). The present communication system may accommodate a large number of implantable devices, e.g., preferably at least 10 and up to 1000 (or more) such devices, which preferably communicate with the SCU 302 in a half duplex manner, i.e., only one device may transmit data at a time across a common communication channel (e.g., a single frequency shared using distinct time slots between multiple devices) or across different communication channels (e.g., multiple frequencies with a different frequency for some or all devices that may or may not additionally share time slots or may be concurrently be transmitted). Additionally, data is typically directed from the SCU 302 to only one implantable device at a time. Accordingly, if the XMTR 168 and RCVR 114b are only powered during time periods proximate to their use, their average power consumption (i.e., their incremental power consumption contribution) may be reduced (relative to the power consumed when all circuitry is active) by a factor of N, where N approaches the maximum number of devices that may be accommodated by the communication protocol. (Actually, the power savings may approach 2×N since the XMTR 168 need not be powered during use of the RCVR 114b and vice versa.)

The communication protocol is preferably configured to enable communication with N, typically greater than 256 devices, e.g., 1000 devices (or more). However, less devices may be used than allotted for in the communication protocol. For example, 10 devices may be used with a communication protocol that allocates time slots for 1000 devices. It is noteworthy that with embodiments of the present invention, it is the communication protocol and not the actual number of devices in the system that determines the percentage power savings of each implantable device 100. For example, if the peak current drain of the XMTR 168 and the RCVR 114b are each 2 ma and the communication protocol accommodates 1000 devices, the average current drain for each device may each be reduced to approximately 2 µa, 0.1% of its peak power, even if fewer devices are actually used in the system. Even allocating as few as 10 time slots in the communication protocol can reduce the average power consumption of the communication related portions to 10% of its peak power.

The communication protocol 400 of FIG. 9 is primarily comprised of (1) a header portion 402, (2) a control data portion 404, (3) a response delay portion 406, and (4) a response data portion 408, resulting in a communication cycle duration 409 and a repetition rate of:

1/(communication cycle duration)

Note that the response data portion 408 (not drawn to scale) in the preferred mode is typically smaller than the control data portion 404 since each of the time slots in the response data portion 408 is typically smaller, e.g., 16 bits, than the time slots in the control data portion 404, e.g., 32 bits.

Collectively, the header portion 402 and control data portion 404 are referred to as the system control data message 411 that is transmitted during a system control time period 413. Similarly, the response data portion 408 occurs during a response time period 415. During the header portion 402, the SCU 302 transmits identification information that identifies the SCU 302 (for situations where multiple SCUs may be present) and may additionally transmit assignment data that assigns time slot IDs 410 (see FIG. 10) to the implantable devices 100 (preferably as part of an initialization sequence that correlates the predefined ID 303 with a designated communication time slot) or if an implantable device loses synchronization, the header can be used to resynchronize that specific device.

Preferably, the clock 312 in the SCU 302 (see FIG. 2) is a high precision crystal-controlled oscillator. However, since clock 412 (see FIG. 10), used for controlling the operation of the implantable devices 100, is synchronized with data bit timing from the SCU 302 during each communication cycle, it does not need to be as precise. Accordingly, a lower precision and potentially lower power clock 412 may be used in the implantable device 100 and a retiming controller, e.g., phase-locked loop 414, processes output 416 from the clock 412 and a received data stream 418 from the RCVR 114b to generate a retimed clock 420 during receipt of data from the SCU 302 by the implantable devices 100 (preferably during its time slot designated by its time slot ID 410). The precision of this retimed clock 420 is such that the time slot portions of the communication protocol can be accurately determined by the implantable devices 100 to permit power to be switched off from the XMTR 168 and RCVR 114b circuitry of each implantable device 100 when these functions are not needed and switched back on just for their needed time periods. Preferably, the accuracy of the phase-locked loop 414 is such that the retimed clock 420 will maintain sufficient accuracy for multiple communication cycles 409, e.g., 300 cycles. An alternative, but less preferable mode, is to use sufficiently accurate clocks in both the SCU and the implantable devices which will be sufficiently accurate to maintain their relative synchronized timing.

Preferably, the RCVRs 114b in all of the implantable devices 100 are initially powered on during the header portion 402 (shown as time period 422) until their time slot IDs 410 (see FIG. 10) have been assigned or reassigned as necessary. After this initialization sequence, RCVRs 114b are powered off during the remainder of the system control data message 411, i.e., the control data portion 404, except for their designated time slots. Following this assignment/reassignment process (used as needed), the SCU 302 transmits the control data portion 404 which contains time slots of data, e.g., 32 bits, for each of the implantable devices 100. This data preferably includes a mode portion, e.g., on the order of 8 bits, to instruct the implantable device 100 as to the requested mode and a data portion, e.g., on the order of 8 bits, which specifies what the implantable device 100 is to do within that mode. Additionally, it is preferred that an error correction code, e.g., on the order of 16 bits, for example using a Reed Muller code, be included with the data sent to each implantable device. Preferably, the data for each implantable device 100 is sent in order, e.g., from lowest time slot ID to highest time slot ID or vice versa. Thus, in FIG. 9, data is sent in time slot 1 of the control data portion 404 to implantable device 1, time slot 2 to implantable device 2, etc. Since, implantable device 1 does not require the information being transmitted to implantable device 2, power may be removed from the RCVR 114b of implantable device 1 shortly after receive time slot 1. This is shown as a time period 424 (see FIG. 9) corresponding to receiver power supply enable 426 (see FIG. 10). Similarly, power to the RCVR 114b of implantable device 2 may be provided only for a time period 428 proximate to receive time slot 2.

Power is similarly applied to the RCVR 114*b* of implantable device N during time period 430.

The receiver power enable signal 426 is generated by a power control circuit 432 (see FIG. 10) which provides power to the RCVR 114*b* in response to the time slot ID 410 of the implantable device 100 and the corresponding receive time periods, e.g., 422 and 424 for implantable device 1, according to the retimed clock 420. Since there may be some "warm up" time associated with the RCVR 114*b* and since it is desirable to adjust the sensitivity of the receiver 114*b* according to the received signal strength using an automatic gain control (AGC) 434, the receiver power enable signal 426 preferably begins shortly before the associated receive time slot and may extend a short period of time afterwards, e.g., a portion of a receive time slot, to allow, for example, for a more efficient lower power drain off control signal. The RCVR 114*b* is powered for a small portion, e.g., less than about 10% for a communication protocol supporting a system of 10 or more implantable devices, of the control data portion 404 of the communication protocol 400. Accordingly, the power consumption associated with the RCVR 114*b* is reduced during the control data portion 404 by a factor approaching N. For example, if the communication protocol supports up to 1000 time slots for up to 1000 implantable devices 100, the power consumption of each implantable device 100 is reduced by a factor of approximately 1000, e.g., 0.1%, independent of the actual number of implantable devices 100 in the system.

Power is also saved in the SCU 302 during this transmit portion of the communication cycle 409 using techniques and circuitry analogous to that already described in reference to the implantable device 100. First, since the SCU only transmits during this period, its receiver 306 is disabled. Second, there is generally not a device N or N−1, etc., in a system. Accordingly, since the assigned devices will generally be grouped from device 1 to device X, e.g., 10, the control data may be transmitted in a burst, terminating prior to the end of the control data portion 404. The time period 431 corresponds to the period of time that power is supplied to the transmitter 304 in the SCU 302. Time period is shown terminating in a dashed line to show that it may not need to extend to the end of control data portion 404. Additionally, since the transmitter 304 is powered in a burst, the inefficiencies associated with cycling its power per device are avoided.

Depending upon the operating mode data sent to each implantable device 100, the implantable device 100 may need time to respond to a stimulation, sense or status request command by sending response data to the SCU 302. This response data, e.g., 16 bits, preferably includes a value portion, e.g., 8 bits, and an error correction code portion, e.g., on the order of 8 bits of Nordstrom Robinson code. Accordingly, the response delay portion 406 is allocated by the communication protocol (additionally saving power in the SCU 302 since neither its transmit or receive circuitry is enabled during that time period) during a time period prior to the response data portion 408. In a manner similar to that previously described for the RCVR 114*b*, power consumption of the XMTR 168 is minimized during the response data portion 408 of the communication protocol. During the response data portion 408, the XMTR 168 is turned on by the power control circuit 432 via a transmit power enable signal 436 during a time period proximate to a time slot determined by the time slot ID 410 of the implantable device 100. Preferably, the transmit power enable signal 436 begins shortly before the ID 410 determined time slot and may extend briefly afterwards. Such transmit power enable signals 436 are shown as extending for time period 438 for time slot 1, 440 for time slot 2, 442 for time slot 3, etc. Each communication channel time slot has a guard band 456, e.g., 10% of the time slot duration, between consecutive response data time slots. While this guard band 456 exists between each time slot, it is only shown for example in time slot 1 of FIG. 9. This guard band must be bigger than the maximum combined drift of the clocks of adjacent implantable devices 100. The XMTR 168 is powered for a small portion, e.g., less than about 10% for a communication protocol supporting a system of 10 or more implantable devices, of the response data portion 408 of the communication protocol 400. Accordingly, since power to the XMTR 168 is only provided temporally proximate to its slot ID 410 related time period, the average power consumption of the XMTR 168 is reduced during the response data portion 408 by a factor approximating M by cycling power to XMTR 168.

Thus, it may be described that:

$$XMTR_{pca} = (XMTR_{pcp}/M) \times (\text{response data time period/communication cycle time period})$$

$$RCVR_{pca} = (RCVR_{pcp}/N) \times (\text{control data time period/communication cycle time period})$$

where $XMTR_{pca}$ = the average power consumption of XMTR 168, $XMTR_{pcp}$ = the peak power consumption of XMTR 168, $RCVR_{pca}$ = the average power consumption of RCVR 114*b*, $RCVR_{pcp}$ = the peak power consumption of RCVR 114*b*, N = the maximum number of time slots available for the SCU 302 to transmit data to the implantable devices 100, and M = the maximum number of time slots available for implantable devices 100 to transmit data to the SCU 302.

Typically, M=N and when the number of implantable devices in a system are equal to M (and N), the time period associated with the response delay portion equals 0. However, in special cases, described further below, it may be desirable to have a different size M and N to alternatively transfer more data from the SCU 302 and selected implantable devices or to transfer more data from selected implantable devices 100 to the SCU 302.

Figure 11:
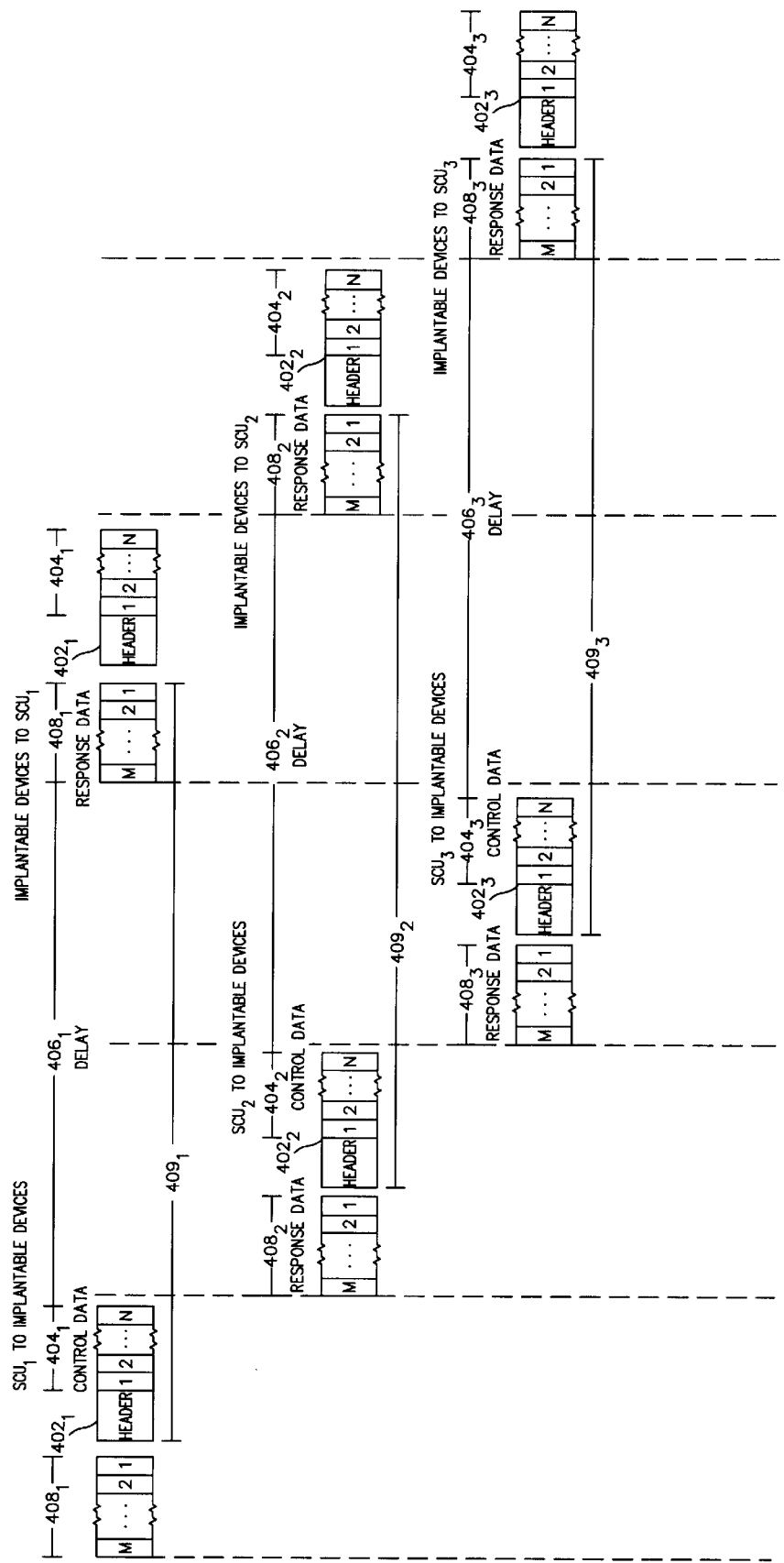
FIG. 11 shows a simplified diagram of multiple systems using the communication protocol of the present invention by intertwining their use of the available communication channel.

While the aforedescribed communication protocol operation and its power saving function are independent of the order that the implantable devices 100 reply to the SCU 302 during the response data portion 408, it is nevertheless preferable that they respond with the highest slot ID device first, e.g., 3, 2, 1. Since there will generally be less than a maximum number of devices in the system, replying in this order will maximize the silence at the beginning of the response data portion 408 and thus effectively extend the response delay portion 406. This extension of the response delay portion 406 may enable multiple systems to operate in the same vicinity without interfering with each other. For example, FIG. 11 displays exemplary timing for a communication protocol 400 that supports up to 1000 time slots/implantable devices used with three subsystems of SCUs 302 and their accompanying group of implantable devices 100. These three SCUs 302 each have a group of up to about 300 implantable devices and the communication protocol 400 permits each of these subsystems to be intertwined on a common communication channel by using the time periods associated with each of their response delay portions 406.

Dashed lines are shown to mark the beginning of each implantable device to SCU response data portion/SCU to implantable device data portion and demonstrates how these time periods of different systems can intertwine successfully.

The controller circuitry 106 and the stimulation and sensor circuitry 110, 188 operate in a manner analogous to that previously described in reference to FIG. 3A. Preferably, the stimulation and sensor circuitry 110, 188 consume minimal power when their functions are not required.

In a manner similar to that previously described in reference to the system control data message 411, power is also saved in the SCU 302 (using circuitry analogous to that already described in reference to the implantable device 100) during the response data portion 408 by having power to the transmitter 304 in the SCU 302 turned off and power to its receiver 306 turned on only during a burst receive time period 443 which extends from the last receive time slot (typically less than slot M) and time slot 1. Accordingly, time period 443 is shown with a dashed leading edge. Additionally, since the receiver 306 is powered in a burst, the inefficiencies associated with cycling its power per device are avoided.

In certain circumstances, it may be desirable to further reduce the power consumption of an implantable device 100 to thus further extend its battery life. In a first alternative mode (time slot sharing), this battery life extension is accomplished by trading off an extended battery life for a decreased communication throughput, but only for individual selected devices that can accommodate the decreased communication throughput. For example, if the duration of the communication cycle 409, i.e., the sum of the time period portions 402, 404, 406, 408, is approximately 10 milliseconds, then the communication rate for each implantable device would be 100 times per second. If the controlled/monitored parameter doesn't require that high of a throughput, e.g., it only requires controlling/monitoring at 25 times per second, then power can be saved by sharing a time slot between multiple devices. In the example shown in FIG. 9, four (4) devices alternately share a time slot 1 during consecutive communication cycles 409 using transmit power periods 438, 444, 446 and 448. Thus, in this example, XMTR 168 would be enabled only ¼ of its 1/M duration of the response data portion 408. Accordingly in this example, the battery life would be extended by an additional factor of 4. If this time slot sharing mode is enabled, this power reduction is available for each device even if not all of the devices are present.

Additionally, there may be a need for a system that has more implantable devices 100 than the aforementioned protocol would otherwise permit. For example, if the communication protocol allocates 1000 time slots, then 1001 or more implantable devices could not be directly supported. However, with the aforementioned first alternative mode, the additional implantable devices may be supported by configuring one or more devices to alternately share a time slot.

To enable this alternative configuration, the SCU 302 preferably includes additional data in the header 402 and/or control data 404 portions to assign implantable devices to portions of a time slot. For example, the SCU may instruct a first implantable device according to its address ID 303 to initialize its time slot ID 410 to time slot 1*a* and a second implantable device to time slot 1*b*. After this initialization, these two implantable devices would alternately share time slot 1, e.g., see for example time periods 438 and 444.

Alternatively, there may be a need to increase the communication rate to one or more of the implantable devices 100. For example, suppose that a body parameter, e.g., a muscle depolarization signal, required more than the exemplary communication rate of 100 samples per second to be adequately measured or controlled, e.g., for fitting purposes. Additionally, suppose that this feature is only needed for a short time, e.g., during an analysis or fitting/calibration mode. While in the previously described first alternative mode, the battery life was extended by decreasing its communication rate, a second alternative mode (implantable device to SCU streaming mode) shortens the battery life to achieve this communication rate enhancement. However, should this operation be required during a fitting period, an external charging magnetic field may be supplied to provide power to the implantable device 100. To enable this second alternative mode, the SCU 302 preferably includes additional data in the header 402 and/or control data 404 portions to assign implantable devices to multiple, preferably consecutive, time slot portions. For example, the SCU 302 may instruct a first implantable device according to its address ID 303 to initialize its time slot ID 410 to time slots 5–54 (see extended time slot period 450) while temporarily disabling any other devices that may have previously been enabled in these time slots. After this initialization, this one implantable device would provide data at 50 times its default data rate but consume 50 times its default transmit power that is otherwise achievable by communication protocol 400. Even so, with an exemplary 1000 slot addressable communication protocol, a 20 fold transmit power savings (1000 slots/50 slots) would still be achieved over systems not practicing the communication protocol of the present invention. Preferably, one or more implantable devices may be configured to operate in this second alternative mode. While this second alternative mode may be extended to enable a single implantable device to communicate during all of the available time slots, it is preferable to not implement this feature if there are implantable devices, e.g., heart pacing devices, that require periodic communications. In such cases, specified time slots, e.g., 1–4, are reserved for these required devices. Preferably, the extra allocated time slots are released under control of the SCU 302 when they are no longer needed and reassigned to other implantable devices.

Generally, communication from the XMTR 168 can occur concurrently with measurements or stimulation using the sensor circuitry 188 or stimulation circuitry 110 via the same set of electrodes 112*a*, 112*b* since the communication frequency used by the XMTR 168 is considerably higher than sensed or stimulated frequencies. (Alternatively, the sensor/stimulation circuitry may use a different set of electrodes 112*c*, 112*d*.) However, in some cases, it may be desirable to alternate sense/stimulate modes with transmit modes. Such an operation is shown as time periods 152 and 154, respectively. Alternatively, while the communication occurs during a portion of the response data portion 408, the associated sensed or stimulated data may be spread/buffered over the duration of the entire communication protocol, e.g., 402, 404, 406, 408, and then communicated in a consolidated burst during one or more time slots during the response data portion 408.

In a third alternative mode (an SCU to implantable device streaming mode), the SCU 302 may, alternatively, allocate multiple time slots, e.g., 452, in the control data portion 404 of the system control data message 411 to a selected implantable device 100 and thus transmit more data in a communication cycle 409 to the selected implantable device 100.

For example, such a high speed transmission of data, e.g., using 90% of the available communication time slots, could be used to send an audio data message by stimulating the patient's auditory nerve. The electrodes could also be hooked up to an implantable sonic transducer (speaker) which could reside in or near the middle ear or under the skin of the patient's middle ear. For example, with a 3 ma battery, 2 ma for the receiver and 2 ma average for stimulation, about 45 minutes of audio would be available. Messages such as "Low Battery", "Five Hours to Battery Depletion", "Move Arm Into Charging Field", etc. would be a useful way to communicate with the patient.

Figure 12A:
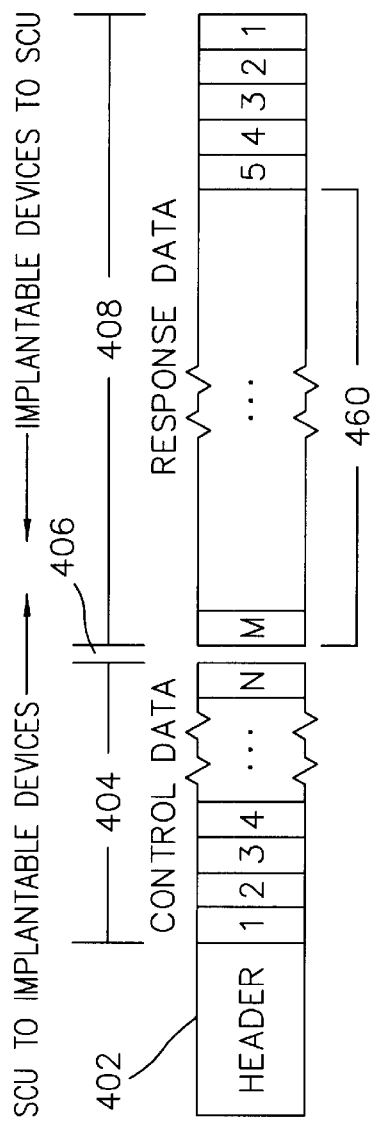
FIGS. 12A and 12B show simplified diagrams of the effects of changing the number of time slots associated with the SCU and the implantable devices.
Figure 12B:
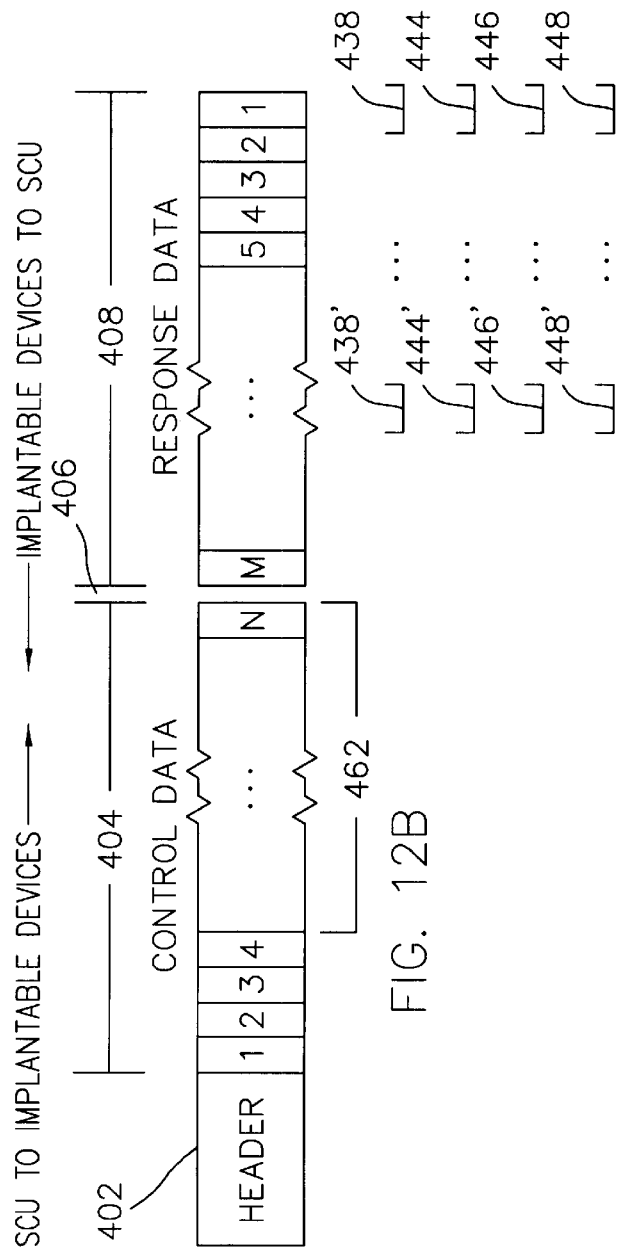

In the first alternative mode (time slot sharing), or second and third alternative modes (the streaming modes), it may be desirable to set the number of SCU to implantable device time slots N be a different value than the number of implantable device to SCU time slots M. For example, in FIG. 12A, the value of M has been increased to a value greater than N such that the response delay time period 406 approaches zero. If an implantable device to SCU streaming mode is needed to provide a higher transfer rate, this implantable device to SCU streaming mode is enabled to dedicate a large number of time slots (see 460) for this communication. Conversely, as shown in FIG. 12B, the value of N has been increased to a value greater than M such that the response delay time period 406 approaches zero. If an SCU to implantable device streaming mode is needed to provide a higher transfer rate, this SCU to implantable device streaming mode is enabled to dedicate a large number of time slots (see 462) for this communication. Additionally, modes can be envisioned where a high control rate is needed for a large number of implantable devices 100 with only a slow rate of feedback from the implantable devices 100 is needed. Accordingly, N would be made larger than M and the previously described slot sharing mode would be implemented.

Preferably, the receiver 306 and/or transceiver 314 in each SCU 302 periodically scan the available spectrum, e.g., from 0.1 MHz to 1000 MHz to look for noisy or less noisy portions of the spectrum. (The scan range may be restricted in varying geographical regions to conform to regional regulations.) Preferably, the SCU 302 periodically, e.g., when the patient goes to a new location, uses this spectrum data to select a less noisy portion of the spectrum, if available. Preferably, the SCU 302 transmits a message to the implantable devices 100 to reassign the operation frequency channel used by its associated group of devices to the less noisy portion of the spectrum.

Figure 13:
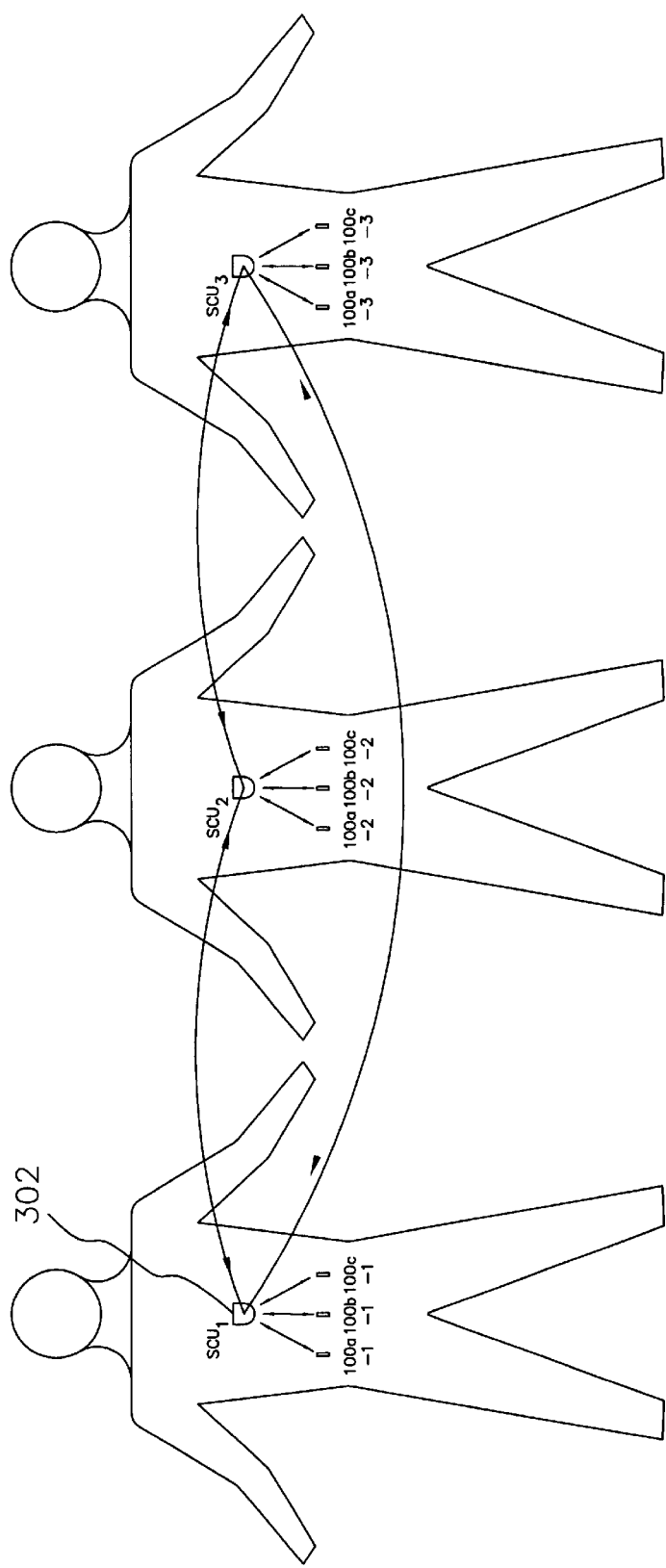
FIG. 13 shows a simplified diagram of the interrogation between a plurality of systems, i.e., SCUs and implantable devices, to allow the systems to coexist in a restricted location.

Preferably, the present system can accommodate multiple systems in a common environment, e.g., if there are two patient's with implantable devices that are in close proximity. Preferably, the transmitter in each SCU 302 will be designed to transmit further than the transmitter in the implantable device 100. The receiver of the SCU 302 will preferably be more sensitive than the receiver in the implantable device 100. When two or more patients are present with this system (see FIG. 13), the SCUs 302 will detect each other by a unique communication channel, and will prioritize each other, e.g., by the ID of each SCU 302 (most preferable), a number from a random number generator 318 (see FIG. 2), other unique numbering scheme, etc. The highest priority SCU will then indicate its receive/transmit time period and request that the next lower priority SCU retime the start of its communication cycle 409. This next lower SCU will then indicate to the next lower SCU to do the same, etc.

If there is insufficient response delay time for the next lowest SCU, that SCU can communicate to highest priority SCU to increase the response delay time 406. The highest priority SCU can then reassign time slots by doubling or tripling time slots, etc., as previously described, for those implantable devices having less critical cycle requirements. Preferably, to plan for this contingency, the less critical devices will be assigned to time slots closest to the delay period 406, e.g., the highest numbered devices as shown in FIG. 9. See, for example FIG. 11, which shows how multiple, e.g., three (3) systems with their associated SCU and implantable devices can each, according to the communication protocol of the present invention, intertwine their use of the communication protocol and thus coexist. For systems where more than one communication channel is available, different system control units can operate in the same time slots but in a different communication channel (see, for example, commonly-assigned, copending U.S. patent application entitled "Combined Frequency-Domain Multiplexing Of Radio Frequency Communications With Multiple Implanted Devices," which is incorporated herein by reference in its entirety).

While the invention herein disclosed has been described by means of specific embodiments and applications thereof, numerous modifications and variations could be made thereto by those skilled in the art without departing from the scope of the invention set forth in the claims. For example, while a preferred embodiment of the communication protocol of the present invention supports communication by the SCU 302 with ten (10) or more implantable devices 100, resulting in reducing the average power consumption of the transmit/receive circuitry to 10% or less of their peak power, the present communication protocol will also provide benefit even if the protocol only supported two (2) or more devices, resulting in reducing the average power consumption to 75% or less of its peak power. A two slot embodiment of the communication protocol could potentially reduce the average power consumption to ½ or 50% of the peak power. However, due to previously described need to power transmit and receive circuitry for time periods slightly greater than their associated time slots, a 50% reduction will not be achieved. This greater average power consumption value is only intended to be an approximate value that reflects this limitation. Additionally, while communications between the SCU and implantable devices has been primary described as occurring on a common communication frequency, embodiments where different communication frequencies are used for each of the time slots associated with each implantable device, e.g., a spread spectrum type implementation, are also considered to be within the scope of the present invention. Such variations are considered to be within the scope of the present invention. It is therefore to be understood that within the scope of the claims, the invention may be practiced otherwise than as specifically described herein.

What is claimed is:

1. A communication protocol for communicating between a system control unit and a plurality of battery-powered, implantable stimulation/sensor devices that is configured to extend the battery life of said implantable devices by reducing their average power consumption, wherein each said implantable device has an address, said communication protocol comprising:

a system control time period for transmitting a system control data message from said system control unit to said plurality of implantable devices, wherein said system control data message contains addressable data to said implantable devices which are selectively enabled to operate in a receive mode in a selected receive portion of said system control time period related to the address of each implantable device, wherein said implantable devices additionally consume a first incremental amount of power when operating in said receive mode, each said selected receive portion of said system control time period being less than 75% of said system control time period and the average power consumption of said implantable devices is reduced accordingly;

a response time period following each system control time period for enabling selected ones of said implantable devices to individually operate in a transmit mode to transmit data to said system control unit in a selected transmit portion of said response time period related to the address of each implantable device, wherein said implantable devices additionally consume a second incremental amount of power when operating in said transmit mode;

a response delay time period between said system control time period and said response time period; and wherein said system control time period, said response time period and said response time period define a communication cycle which periodically repeats at a repetition rate.

2. The communication protocol of claim 1 wherein each said selected transmit portion of said response time period is less than 75% of said response time period and the average power consumption of said implantable devices is reduced accordingly.

3. The communication protocol of claim 1 wherein each said selected transmit portion defines a time slot and at least one said selected transmit portion of said response time period used by at least one said implantable device to transmit data to said system control unit is related to the address of said implantable device and data within said system control data message.

4. The communication protocol of claim 3 wherein at least one of said implantable devices is assigned to a selected one of said time slots by data transmitted from said system control unit.

5. The communication protocol of claim 3 wherein each time slot additionally comprises a guard band for providing a time period between adjacent time slots when adjacently assigned implantable devices do not transmit data.

6. The communication protocol of claim 1 wherein:

in a first mode of operation at least one said selected transmit portion of said response time period is used for responses from a single implantable device; and in a second mode of operation at least one said selected transmit portion of said response time period is configurable to be shared during alternate communication cycles for transmitting responses to said system control unit from a plurality of said implantable devices, thereby extending the battery life of said implantable devices that are configured to share said selected response time period portions.

7. The communication protocol of claim 1 wherein said addressable data of said system control data message is transmitted at a rate defining a bit rate and said transmitted bit rate of said system control data message determines timing of said selected transmit portions of said response time period for transmitting data from said implantable devices to said system control unit.

8. The communication protocol of claim 1 wherein:

in a first mode of operation at least one of said selected implantable devices operates in a transmit mode during a single selected transmit portion of said response time period; and in a second mode of operation at least one selected implantable device operates in a transmit mode during a plurality of selected transmit portions of said response time period, thereby increasing the amount of data that may be transmitted from said at least one selected implantable device during each communication cycle.

9. The communication protocol of claim 8 wherein in said second mode of operation at least one selected implantable device operates in a transmit mode during a plurality of consecutive selected transmit portions of said response time period.

10. The communication protocol of claim 1 wherein said communication cycle is essentially fixed and said communication protocol supports a predetermined number of communication slots, wherein said predetermined number of communication slots determines the average power consumption reduction; and wherein said system control time period and said response time period decrease and said response delay time period increases when an actual number of implantable devices within a system is decreased relative to said predetermined number of communication slots.

11. The communication protocol of claim 10 wherein when said actual number of implantable devices is less than said predetermined number of communication slots, a system having multiple system control units each operating according to said communication protocol is supported by sharing said increased response delay time periods associated with another one of said system control units.

12. The communication protocol of claim 1 wherein said system control data time period and said response data time period are each comprised of time slots and said system control message communicates in a first numerical time slot order with said implantable devices and said implantable devices communicate with said system control unit in a second numerical order wherein said second order is the opposite of said first order.

13. The communication protocol of claim 12 wherein said first numerical time slot order is in ascending order.

14. The communication protocol of claim 1 wherein each said selected transmit portion defines a time slot and each implantable device communicates with said system control unit using a different frequency during its associated time slot.

15. The communication protocol of claim 1 wherein the system control message is configurable to direct a plurality of addressable data portions to a selected one of said implantable devices, thereby increasing the communication rate from said system control unit to said selected implantable device.

16. The communication protocol of claim 15 wherein said selected implantable device is suitable for providing an auditory message to a patient.

17. A system for programmably controlling the operation of a plurality of battery-powered, implantable stimulation/sensor devices that is configured to extend the battery life of said implantable devices by reducing their average power consumption, said system comprising:

one or more battery-powered implantable device wherein each of said devices has an identification address;

a system control unit for periodically sending, during a system control time period, a system control message containing addressable data directed to each of said implantable devices, wherein each said system control message is followed by a response time period for enabling each of said implantable devices to transmit data to said system control unit, wherein said implantable devices are selectively enabled to operate in a receive mode in a selected receive portion of said system control time period related to the address of each implantable device, wherein said implantable devices additionally consume a first incremental amount of power when operating in said receive mode, each said selected receive portion of said system control time period being less than 75% of said system control time period and the average power consumption of said implantable devices is reduced accordingly; and wherein said implantable devices individually operate in a transmit mode to transmit data to said system control unit in a selected portion of said response data time period related to the address of each implantable device, wherein said implantable devices additionally consume a second incremental amount of power when operating in said transmit mode.

18. The system of claim 17 wherein each said selected transmit portion of said response time period is less than 75% of said response time period and the average power consumption of said implantable devices is reduced accordingly.

19. The system of claim 17 wherein at least one said selected transmit portion of said response time period used by at least one said implantable device to transmit data to said system control unit is related to the address of said implantable device and data within said system control data message.

20. The system of claim 17 wherein:

in a first mode of operation at least one said selected transmit portion of said response time period is used for responses from a single implantable device; and in a second mode of operation at least one said selected transmit portion of said response time period is configurable to be shared during alternate communication cycles for transmitting responses to said system control unit from a plurality of said implantable devices, thereby extending the battery life of said implantable devices that are configured to share said selected response time period portions.

21. The system of claim 17 wherein said system control unit operates according to a system control unit clock and each said implantable devices operate according to an implantable device clock and wherein each of said clocks are relatively accurate to maintain communication timing between each of said devices.

22. The system of claim 17 wherein said addressable data of said system control data message is transmitted at a rate defining a bit rate timing and said transmitted bit rate timing of said system control data message determines timing of said selected transmit portions of said response time period for transmitting data from said implantable devices to said system control unit.

23. The system of claim 22 wherein each said implantable device additionally comprises a retiming controller for synchronizing its timing for selected transmit portions of said response time period to said transmitted bit rate timing of said system control data message.

24. The system of claim 23 wherein said retiming controller comprises a phase locked loop.

25. The system of claim 17 wherein:

in a first mode of operation at least one of said selected implantable devices operates in a transmit mode during a single selected transmit portion of said response time period; and in a second mode of operation at least one selected implantable device operates in a transmit mode during a plurality of selected transmit portions of said response time period, thereby increasing the amount of data that may be transmitted from said at least one selected implantable device during each response time period.

26. The system of claim 25 wherein in said second mode of operation at least one selected implantable device operates in a transmit mode during a plurality of consecutive selected transmit portions of said response time period.

27. The system of claim 17 wherein each said implantable device additionally comprises a magnetoresistive sensor for sensing a magnetic field from a source external to a patient's body and wherein in response to sensing said magnetic field, operation of said implantable device is altered.

28. The system of claim 27 wherein said altered operation of said implantable device comprises removing power from one or more portions of said implantable device, thereby reducing the power consumption of said device.

29. The system of claim 17 wherein said system control unit comprises:

a system controller for controlling operation of said system control unit;

a transmitter for transmitting data from said system control unit to one or more of said implantable devices, wherein power is only supplied to said transmitter during said system control time period;

a receiver for receiving data from one or more or said implantable device, wherein power is only supplied to said receiver during said response time period; and wherein the average power consumption of said system control unit is reduced.

30. The system of claim 29 wherein said power supplied to said transmitter is supplied in a burst to enable data transmission during said system control time period and said power supplied to said receiver is supplied in a burst to enable data reception during said response time period.

31. The system of claim 29 wherein power consumption by said transmitter is minimized during time periods outside of said system control time period and power consumption of said receiver is minimized during time periods outside of said response time period.

32. The system of claim 29 wherein:

said system controller periodically instructs said transmitter to transmit an inquiry message to notify an other system controller of its presence and interrogates said receiver if an inquiry message has been received to determine the presence of said other system control unit; and wherein in response to receipt of an inquiry message said system control unit negotiates a communication parameter change with said other system control unit and notifies said associated implantable devices to alter said communication parameter to thereby avoid the effects of the presence of said other system control unit.

33. The system of claim 32 wherein each of said system control units has an identification value and said negotiated communication parameter change is dependent upon said identification values related to each of said system control units.

34. The system of claim 32 wherein at least one of said system control units additionally comprised a random number generator and said negotiated communication parameter change is dependent upon said at least one random number generator.

35. The system of claim 32 wherein said negotiated communication parameter change comprises a difference in communication phase with each system control unit and its associated implantable devices.

36. The system of claim 32 wherein said negotiated communication parameter change comprises a difference in communication frequency with each system control unit and its associated implantable devices.

37. The system of claim 32 wherein said negotiated communication parameter change comprises a time slot alteration for communication between at least one of said system control units and at least one of its associated implantable devices.

38. The system of claim 32 wherein said system control unit and said implantable devices operate across a first communication channel and communications between said system controllers is on a second communication channel separate from said first communication channel.

39. The system of claim 38 wherein said communication across said second communication channel comprises a higher radiated transmission power than across said first communication channel.

40. The system of claim 39 wherein said receiver in said system control unit has increased sensitivity to received data across said second communication channel.

41. The system of claim 38 wherein said communication across said second communication channel occurs within a different frequency range from said first communication channel.

42. The system of claim 17 wherein said system control unit and said implantable devices operate across a common communication frequency channel.

43. The system of claim 17 wherein said implantable devices communicate with said system control unit across a plurality of frequency channels.

44. A method of communicating between a system control unit and a plurality of addressable, battery-powered, implantable stimulation/sensor devices wherein said method is configured to extend the battery life of said implantable devices by reducing their average power consumption and wherein each said implantable device has an address, said method comprising the steps of:
  periodically, during a system control time period, sending a system control message which defines addressable data that is to be directed to each of said plurality of implantable devices, wherein said implantable devices consume a base amount of power and additionally consume a first incremental amount of power when operating in a receive mode to receive data from said system control unit; and
  waiting a response time period following each system control message for enabling each of said implantable devices to provide data to said system control unit in a selected transmit portion of said response time period related to the address of each implantable device, wherein said implantable devices additionally consume a second incremental amount of power when operating in said transmit mode, said selected transmit portion of said response time period being less than 75% of said response time period and the average power consumption of said implantable devices is reduced accordingly.

45. The method of claim 44 further comprising the step of switching between a first mode of operation where at least one said selected transmit portion of said response time period is used for responses from a single implantable device and a second mode of operation where said at least one selected transmit portion of said response time period is configurable to be alternately shared for sending responses to said system control unit from a plurality of said implantable devices, thereby extending the battery life of said implantable devices that are configured to share said selected response time period portions.

46. The method of claim 44 further comprising the step of determining the timing of said selected transmit portions of said response time period for providing data from said implantable devices to said system control unit according to a bit rate of said system control message.

47. The method of claim 44 further comprising the step of enabling said receive mode of said implantable devices during time periods proximate to selected portions of said system control message related to the address of each implantable device wherein each said receive mode of said implantable device is enabled for less than 75% of said system control message and the average power consumption of said implantable device is reduced accordingly.

48. The method of claim 47 further comprising the step of switching between a first mode of operation where said selected transmit portion of said response time period is used for responses from a single implantable device and a second mode of operation where said selected transmit portion of said response time period is configurable to be alternately shared for sending responses to said system control unit from a plurality of implantable devices, thereby extending the battery life of said implantable devices that are configured to share said selected response time period portions.

49. The method of claim 47 further comprising the step of determining the timing of said implantable devices entering into said receive mode according to a bit rate of said system control message.

50. The method of claim 44 additionally comprising the steps of:
  periodically sending an inquiry message to an other system control unit;
  periodically receiving any inquiry message from said other system control unit;
  negotiating a communication parameter change with said other system control unit if said inquiry message is received; and
  sending a message from said system control unit to said implantable devices to alter its negotiated communication parameter change to avoid the effects of the presence of said other system control unit.

51. The method of claim 44 additionally comprising the steps of:
  periodically interrogating a predetermined frequency spectrum range to determine noise levels; and
  periodically sending a message from said system control unit to said implantable devices to alter its communication frequency with said system control unit according to said determined noise levels.

52. A communication protocol for communicating between a system control unit and a plurality of addressable, battery-powered, implantable stimulation/sensor devices that is reconfigurable to alternatively extend the battery life of said implantable devices by reducing their average power consumption or increasing the effective communication rate between said system control unit and said implantable device, said communication protocol comprising:
  a system control message for defining addressable data to be directed to each of said plurality of implantable devices operating in a receive mode, wherein said implantable devices consume a base amount of power and additionally consume a first incremental amount of power when operating in said receive mode;
  a response time period following each system control message for enabling each of said implantable devices to individually operate in a transmit mode to provide data to said system control unit in a selected portion of said response time period related to the address of each implantable device, wherein said implantable devices additionally consume a second incremental amount of power when operating in said transmit mode, said selected portion of said response time period being less than 75% of said response time period and the average power consumption of said implantable devices is reduced accordingly; and wherein at least one selected implantable device is configurable via data within said system control message to occupy a plurality of said selected portions of said response time period to thereby increase the effective communication rate from said implantable device to said system control unit.

53. The communication protocol of claim 52 wherein:

in a first mode of operation at least one said selected portion of said response time period is used for responses from a single implantable device; and in a second mode of operation said selected portion of said response time period is configurable to be alternately shared for sending responses to said system control unit from a plurality of implantable devices, thereby extending the battery life of said implantable devices that are configured to share said selected time response period portions.

54. The communication protocol of claim 52 wherein said addressable data of said system control message is transmitted at a rate defining a bit rate and said transmitted bit rate timing determines timing of said selected portions of said response time period for providing data from said implantable devices to said system control unit.

55. The communication protocol of claim 52 wherein a plurality of said implantable devices operate in said receive mode during selected portions of said system control message related to the address of each implantable device.

56. The communication protocol of claim 55 wherein:

in a first mode of operation at least one said selected portion of said response time period is used for responses from a single implantable device; and in a second mode of operation said selected portion of said response time period is configurable to be alternately shared for sending responses to said system control unit from a plurality of implantable devices, thereby extending the battery life of said implantable devices that are configured to share said selected time period portions.

57. The communication protocol of claim 55 wherein said addressable data of said system control message is transmitted at a rate defining a bit rate and said transmitted bit rate timing determines timing of said implantable devices for entering into said receive mode.

58. The communication protocol of claim 52 wherein the system control message is configurable to direct a plurality of addressable data portions to a selected one of said implantable devices, thereby increasing the communication rate from said system control unit to said selected implantable device.

* * * * *

UNITED STATES PATENT AND TRADEMARK OFFICE
CERTIFICATE OF CORRECTION

PATENT NO. : 6,472,991 B1 Page 1 of 1
DATED : October 29, 2002
INVENTOR(S) : Schulman et al.

It is certified that error appears in the above-identified patent and that said Letters Patent is hereby corrected as shown below:

Column 21,
Line 21, should read as follows:
-- and said response delay time period define a communication --

Signed and Sealed this

Twelfth Day of October, 2004

JON W. DUDAS
*Director of the United States Patent and Trademark Office*